(12) United States Patent
Hyde et al.

(10) Patent No.: US 9,808,579 B2
(45) Date of Patent: Nov. 7, 2017

(54) NEEDLELESS INJECTOR SYSTEMS, AND RELATED METHODS AND COMPONENTS

(71) Applicant: Elwha LLC, Bellevue, WA (US)

(72) Inventors: Roderick A Hyde, Redmond, WA (US); Muriel Y. Ishikawa, Livermore, CA (US); Eric C. Leuthardt, St. Louis, MO (US); Lowell L. Wood, Jr., Bellevue, WA (US); Victoria Y. H. Wood, Livermore, CA (US)

(73) Assignee: ELWHA LLC, Bellevue, WA (US)

( * ) Notice: Subject to any disclaimer, the term of this patent is extended or adjusted under 35 U.S.C. 154(b) by 244 days.

(21) Appl. No.: 13/889,438

(22) Filed: May 8, 2013

(65) Prior Publication Data

US 2014/0336561 A1 Nov. 13, 2014

(51) Int. Cl.
*A61M 5/30* (2006.01)
*A61L 2/00* (2006.01)
(Continued)

(52) U.S. Cl.
CPC .............. *A61M 5/30* (2013.01); *A61L 2/00* (2013.01); *A61L 2/24* (2013.01); *A61L 2/02* (2013.01);
(Continued)

(58) Field of Classification Search
CPC .... A61M 5/30; A61M 5/3007; A61M 5/3015; A61M 39/16; A61M 36/162; A61M 2039/167; A61L 2/00; A61L 2/0011; A61L 2/0029; A61L 2/0058; A61L 2/0047; A61L 2/0082; A61L 2/0088; A61L 2/0094

USPC .... 604/158–164.01, 164.04, 164.06, 164.07, 604/164.08, 164.09, 164.1, 164.11, 604/165.01, 165.02, 165
See application file for complete search history.

(56) References Cited

U.S. PATENT DOCUMENTS 2,627,269 A * 2/1953 McGregor .............. A61M 5/31
215/390
3,593,423 A * 7/1971 Jones et al. ..................... 433/80
(Continued)

FOREIGN PATENT DOCUMENTS

WO WO 2008/001377 A2 1/2008

OTHER PUBLICATIONS

PCT International Search Report; International App. No. PCT/US2014/036740; dated Sep. 1, 2014; pp. 1-8.
(Continued)

*Primary Examiner* — Kevin C Sirmons
*Assistant Examiner* — William Carpenter
(74) *Attorney, Agent, or Firm* — Dorsey & Whitney LLP

(57) ABSTRACT

Embodiments disclosed herein are directed to systems and methods for protecting needleless injector units from one or more contaminants. In an embodiment, a needleless injector system includes a needleless injector unit and an auxiliary unit. The needleless injector unit has a nozzle portion and a supply of one or more substances for injection. The needleless injector unit is configured to inject the one or more substances from the nozzle portion through a skin surface of a subject. The auxiliary unit is coupleable to the needleless injector unit. The auxiliary unit includes a source of one or more protectants and is configured to emit the one or more protectants in a region between the nozzle portion of the needleless injector unit and the skin surface of the subject.

45 Claims, 10 Drawing Sheets

(51) Int. Cl.
*A61L 2/24* (2006.01)
*A61M 39/16* (2006.01)
*A61L 2/02* (2006.01)
*A61L 2/16* (2006.01)

(52) U.S. Cl.
CPC .............. *A61L 2/16* (2013.01); *A61M 39/16* (2013.01); *A61M 2039/167* (2013.01)

(56) References Cited

U.S. PATENT DOCUMENTS

| | | | | |
|---|---|---|---|---|
| 3,634,938 | A * | 1/1972 | Hutchinson | 433/29 |
| 3,680,559 | A * | 8/1972 | Gorbahn | A61M 5/3129 |
| | | | | 604/193 |
| 4,515,590 | A * | 5/1985 | Daniel | A61D 1/025 |
| | | | | 604/144 |
| 5,092,864 | A * | 3/1992 | Hayes et al. | 606/10 |
| 5,242,300 | A * | 9/1993 | Esrock | 433/80 |
| 5,275,558 | A * | 1/1994 | Seney | 433/82 |
| 5,388,988 | A * | 2/1995 | Goisser et al. | 433/29 |
| 5,554,172 | A * | 9/1996 | Horner et al. | 607/88 |
| 5,630,796 | A * | 5/1997 | Bellhouse et al. | 604/518 |
| 5,725,875 | A * | 3/1998 | Noll | A01N 25/24 |
| | | | | 424/1.17 |
| 5,746,714 | A | 5/1998 | Salo et al. | |
| 5,817,054 | A * | 10/1998 | Grimm | 604/62 |
| 5,925,036 | A * | 7/1999 | Maxwell, III | A61B 18/24 |
| | | | | 606/13 |
| 6,027,492 | A * | 2/2000 | Vetter | A61B 17/32093 |
| | | | | 600/310 |
| 6,083,197 | A | 7/2000 | Umbaugh | |
| 6,106,516 | A * | 8/2000 | Massengill | 606/15 |
| 6,254,597 | B1 * | 7/2001 | Rizoiu et al. | 606/13 |
| 6,730,113 | B2 * | 5/2004 | Eckhardt et al. | 607/94 |
| 6,802,826 | B1 | 10/2004 | Smoliarov et al. | |
| 7,156,823 | B2 | 1/2007 | Landau et al. | |
| 7,357,781 | B2 | 4/2008 | Menassa | |
| 8,343,130 | B2 | 1/2013 | Green | |
| 8,431,074 | B2 * | 4/2013 | Neer | A61M 39/16 |
| | | | | 422/24 |
| 8,485,818 | B2 * | 7/2013 | Boutoussov | A61C 1/0046 |
| | | | | 433/26 |
| 2002/0086036 | A1 | 7/2002 | Walker | |
| 2002/0107199 | A1 | 8/2002 | Walker | |
| 2004/0267182 | A1 * | 12/2004 | Davis et al. | 604/2 |
| 2005/0214227 | A1 | 9/2005 | Prestrelski et al. | |
| 2005/0256517 | A1 | 11/2005 | Boutoussov | |
| 2007/0118098 | A1 | 5/2007 | Tankovich | |
| 2007/0129693 | A1 * | 6/2007 | Hunter et al. | 604/294 |
| 2007/0156095 | A1 * | 7/2007 | Hazut et al. | 604/173 |
| 2008/0255498 | A1 * | 10/2008 | Houle | A61C 17/02 |
| | | | | 604/20 |
| 2009/0048648 | A1 * | 2/2009 | Dacey, Jr. | A61F 2/30 |
| | | | | 607/88 |
| 2009/0076443 | A1 | 3/2009 | Slate et al. | |
| 2009/0163965 | A1 * | 6/2009 | Boyden | A61F 2/30 |
| | | | | 607/3 |
| 2009/0177139 | A1 * | 7/2009 | Boyden | A61F 2/30 |
| | | | | 604/20 |
| 2010/0025427 | A1 * | 2/2010 | Chiou | B65D 83/262 |
| | | | | 222/1 |
| 2010/0233645 | A1 | 9/2010 | Rizoiu | |
| 2011/0015614 | A1 | 1/2011 | Rykhus, Jr. et al. | |
| 2011/0152790 | A1 * | 6/2011 | Dacey, Jr. | A61F 2/30 |
| | | | | 604/265 |
| 2011/0295232 | A1 | 12/2011 | Slate et al. | |
| 2013/0323684 | A1 * | 12/2013 | Monty | A61C 1/0069 |
| | | | | 433/215 |

OTHER PUBLICATIONS

European Patent Office, Supplementary European Search Report, Pursuant to Rule 62 EPC; App. No. EP 14794481.3; dated Nov. 16, 2016 (received by our Agent on Nov. 23, 2016); pp. 1-7.

* cited by examiner

NEEDLELESS INJECTOR SYSTEMS, AND RELATED METHODS AND COMPONENTS

SUMMARY

Embodiments disclosed herein are directed to systems and methods for protecting needleless injector units from one or more contaminants. In an embodiment, a needleless injector system includes a needleless injector unit and an auxiliary unit. The needleless injector unit has a nozzle portion and a supply of one or more substances for injection. The needless injector unit is configured to inject the one or more substances from the nozzle portion through a skin surface of a subject. The auxiliary unit is coupleable to the needleless injector unit. The auxiliary unit includes a source of one or more protectants, and is configured to emit the one or more protectants in a region between the nozzle portion of the needleless injector unit and the skin surface of the subject.

In an embodiment, an auxiliary system for use in a needleless injector system is disclosed. The auxiliary system includes a coupling mechanism, a needleless injector unit, a source of one or more protectants, and a control unit. The coupling mechanism is configured to securely couple to the needleless injector unit. The needleless injector unit includes a nozzle portion and a supply of one or more substances. The needleless injector unit is configured to inject the one or more substances from the nozzle portion through a skin surface of a subject. The control unit is configured to control injection of the one or more substances from the needleless injector unit and emission of the one or more protectants from the auxiliary system in a region between the nozzle portion of the needless injector unit and the skin surface of the subject.

In an embodiment, a method of administering one or more substances through a skin surface of a subject is disclosed. The method includes injecting the one or more substances from a nozzle portion of a needleless injector unit and through the skin surface of the subject. The method further includes emitting one or more protectants from an auxiliary unit associated with the needleless injector unit.

The foregoing is a summary and thus may contain simplifications, generalizations, inclusions, and/or omissions of detail; consequently, the reader will appreciate that the summary is illustrative only and is NOT intended to be in any way limiting. Other aspects, features, and advantages of the devices and/or processes and/or other living subject matter described herein will become apparent after reading the teachings set forth herein.

DETAILED DESCRIPTION

Figure 1A:
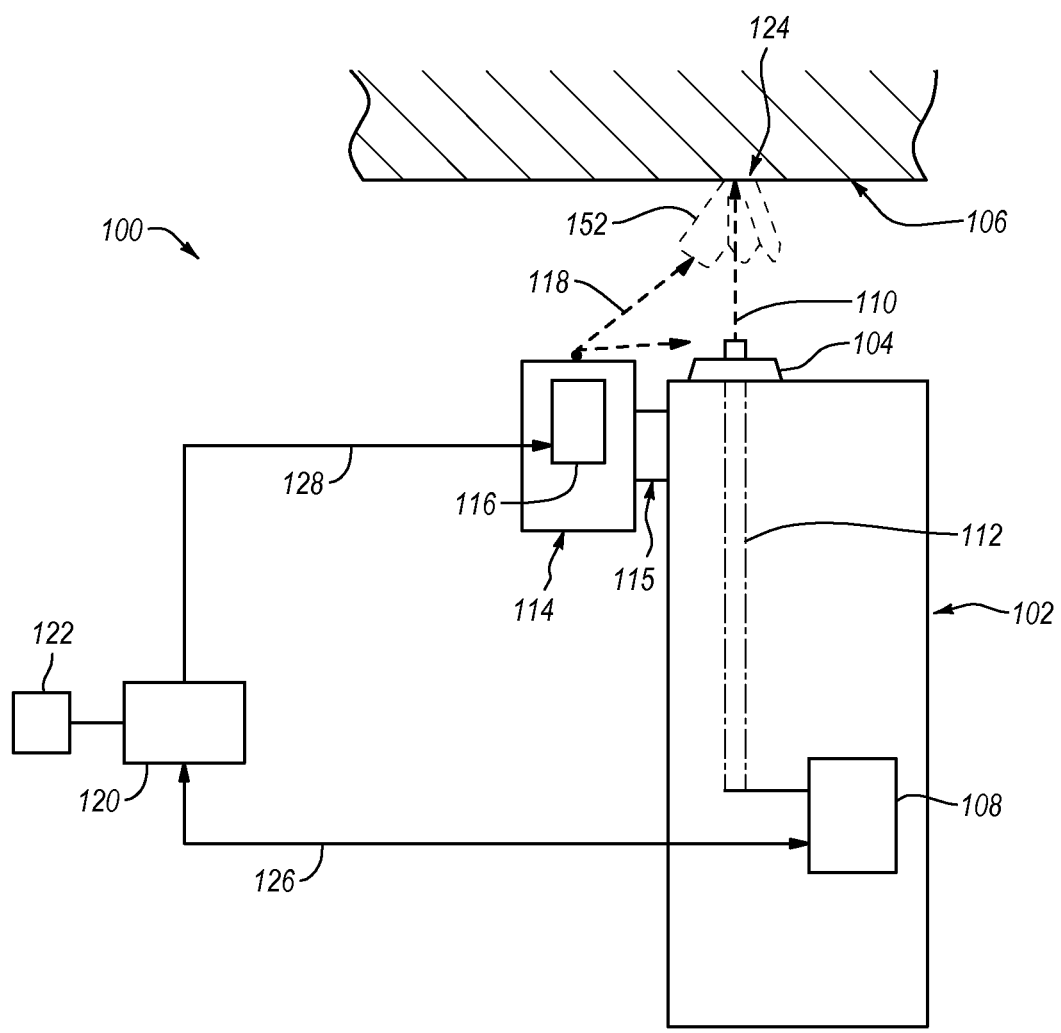
FIG. 1A is a schematic diagram of an embodiment of a needleless injector system.

Embodiments disclosed herein are directed to systems and methods for protecting needleless injectors from one or more contaminants during or immediately following the injection. In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be strictly limiting. Other embodiments may be utilized, and other changes may be made, without departing from the spirit or scope of the subject matter presented herein.

FIG. 1A is a schematic diagram of an embodiment of a needleless injector system 100. The needleless injector system 100 includes a needleless injector unit 102 having a nozzle portion 104 positionable at or near a skin surface 106 of a subject (e.g., a human being or an animal). The needleless injector unit 102 can also include a supply 108 of one or more substances 110 in fluid communication with the nozzle portion 104. For example, the one or more substances 110 can include medicinal or therapeutic substances, such as at least one of antiseptics, vaccines, drugs, nucleotide based (e.g., DNA, RNA) medications, pharmaceutical vehicles or excipients, pain killers, coagulants, hormones, or antibiotics.

The needleless injector unit 102 is configured to inject the one or more substances 110 from the nozzle portion 104 and through the skin surface 106 of the subject. For example, the needleless injector unit 102 can be configured to inject the one or more substances transdermally through the skin surface 106, intradermally through the skin surface 106, subcutaneously through the skin surface 106, or at any suitable depth through the skin surface 106. The needleless injector unit 102 may exhibit a variety of different geometries selected for a particular application. For example, in an embodiment, the needleless injector unit 102 includes a passageway 112 (shown in phantom) in fluid communication with the supply 108 of one or more substances 110 that allows the one or more substances 110 to be injected from the nozzle portion 104 of the needleless injector unit 102.

In an embodiment, the needleless injector unit 102 can include any suitable conventional needleless injector unit. For example, the needleless injector unit 102 can include, but is not limited to The Stratis Injector, commercially available from Pharmajet, Inc., Golden, Colo.; The Biojector 2000, commercially available from Biojet Medical Technologies, Inc., Tigard Oreg.; or The Madajet XL Medical, commercially available from Mada, Inc., Carlstadt, N.J. Other examples of suitable conventional needleless injector units for the needleless injector unit 102 are disclosed in U.S. Pat. Nos. 5,746,714; 6,083,197; 7,156,823; 7,357,781; and 8,343,130, all of which are incorporated herein, in their entirety, by this reference. Of course, other individually adapted needleless injector units may be employed for the needleless injector unit 102.

In an embodiment, the needleless injector unit 102 is configured to clean the nozzle portion after the one or more substances 110 are injected from the nozzle portion 104. For example, the needleless injector unit 102 cleans or clears the nozzle portion 104 with at least one air pulse or multiple air pulses after the nozzle portion 104 is moved away from the skin surface 106.

The needleless injector system 100 further includes an auxiliary unit 114 coupleable to the needleless injector unit 102. In an embodiment, the auxiliary unit 114 is removably coupled to the needleless injector unit 102. In an embodiment, the auxiliary unit 114 is fixedly coupled to the needleless injector unit 102. In an embodiment, the needleless injector system 100 includes a coupling mechanism 115 configured to couple the auxiliary unit 114 to the needleless injector unit 102. The coupling mechanism 115 can physically or operatively couple the auxiliary unit 114 and the needleless injector unit 102 together. In an embodiment, the coupling mechanism 115 includes an attachment lumen on the needleless injector unit 102 that accepts the auxiliary unit 114 to couple the auxiliary unit 114 and the needleless injector unit 102 together. In an embodiment, the coupling mechanism 115 includes one or more snap-in features (e.g., recesses) on the auxiliary unit 114 and one or more protrusions on the needleless injector unit 114. The snap-in features on the auxiliary unit 114 can correspond with protrusions on the needleless injector unit 102, such that the snap-in features snap over the protrusions, thereby securely coupling the auxiliary unit 114 to the needleless injector unit 102. In an embodiment, the needleless injector unit 114 includes the snap-in features and the auxiliary unit includes the one or more protrusions. In an embodiment, the coupling mechanism 115 includes one or more interlocks (e.g., the interlocks 448 shown in FIG. 4A) physically coupling the auxiliary unit 114 to the needleless injector unit 102. In an embodiment, the coupling mechanism 115 includes the auxiliary unit 114 and the needleless injector unit 102 having corresponding locking tapers, such as the auxiliary unit 114 can be coupled and secured to the needleless injector unit 102. Examples of other suitable coupling mechanisms, include, but are not limited to, a hook-and-loop system, magnets, adhesives, snaps, straps, clips, clamps, mechanism fasteners, or welding. In an embodiment, the coupling mechanism 115 includes a control unit (e.g., the control unit 120 shown in FIG. 1A) operatively coupling the auxiliary unit 114 to the needleless injector unit 102.

The auxiliary unit 114 can include a source 116 of one or more protectants 118, and is configured to emit the one or more protectants 118 in a region between the nozzle portion 104 of the needleless injector unit 102 and the skin surface 106. In an embodiment, the auxiliary unit 114 is configured to emit the one or more protectants 118 to protect at least the nozzle portion 104 of the needleless injector unit 102 from one or more contaminants 152. In an embodiment, the auxiliary unit 114 includes a nozzle portion from which the one or more protectants 118 can be emitted.

In an embodiment, the one or more contaminants 152 includes a material released from the skin surface 106 or from beneath the skin surface 106, which may come into contact with any part of the needleless injector unit 102, including contact with the nozzle portion 104. The one or more contaminants 152 includes, for example, at least one of a biological material from the subject, a molecule, a hazardous material, blood from the subject, dirt, a chemical substance, cellular debris from the subject, a cell, biological fluid from the subject, bacteria, a virus from the subject, or medication ejected, projected or otherwise released from the skin surface 106 or from beneath the skin surface during injection of the one or more substances 110 that can contaminate the needleless injector unit 102, or the nozzle portion 104 and can be transferred from one subject to the next.

In an embodiment, at least one of the one or more protectants 118 includes a gas, a liquid, or a solid phase material. In an embodiment, at least one of the one or more protectants 118 includes a disinfectant, an oxidizer, an acid, a base, an adhesive, electromagnetic radiation, a neutralizer, air, or water. In an embodiment, at least one of the one or more protectants 118 substantially entraps, entrains, or otherwise captures the one or more contaminants 152. Examples of the one or more protectants 118 that can substantially entrap, entrain, or otherwise capture the one or more contaminants 152 include, but are not limited to, hydrogel material, air, water, or a gas stream. In an embodiment, at least one of the one or more protectants 118 provides the target region 124 on the skin surface 106. Examples of protectants that can provide the target region 124 include, but are not limited to, a chemical dye, a fluorescent dye (e.g., fluorescein), methylene blue, ink, or a tag.

In an embodiment, at least one of the one or more protectants 118 adheres to the skin surface 106. Examples of protectants 118 that can adhere to the skin surface 106 include, but are not limited to, a bandage adhesive, a tissue adhesive, a thin polymer adhesive, a bioadhesive, a synthetic adhesive, cyanoacrylate, polyvinylpyrrolidone, or polyethylene glycol. In such an embodiment, the one or more protectants 118 prevent or limit movement of the one or more contaminants 152 in a first direction substantially away from the skin surface 106 by forming a barrier on the skin surface 106 that captures the one or more contaminants 152. For example, injection pressure of the one or more substances 110 can be selected so that the one or more substances 110 penetrate through the barrier and the skin surface 106, while the resultant one or more contaminants 152 moving in the first direction away from skin are caught by the barrier. In an embodiment, the barrier includes the target region 124 and a small concentration of methylene blue, allowing visualization of the target region 124. In an embodiment, the one or more substances 110 pass through the barrier or target region 124 in a first direction and the one or more protectants 118 in a second direction.

In an embodiment, the one or more protectants 118 can be emitted into the air space between the nozzle 104 and the skin surface 106, onto the skin surface 106, or through the skin surface 106. In an embodiment, at least one of the one or more protectants 118 substantially seals the nozzle portion 104 against the skin surface 106. Examples of the one or more protectants 118 that can substantially seal the nozzle portion 104 can include, but are not limited to, surgical sealants, glues, or cyanoacrylates.

In an embodiment, at least one of the one or more protectants 118 substantially neutralizes the one or more contaminants 152. Examples of protectants 118 that can substantially neutralize at least one of the one or more contaminants 152 include, but are not limited to an acid, such as citric acid, sodium bicarbonate, bisulfate, or commercial available chemical neutralizers. In an embodiment, at least one of the one or more protectants 118 at least partially disinfects or cleans the nozzle portion 104 of the needleless injector unit 102. Examples of the one or more protectants 118 that can at least partially disinfect or clean the nozzle portion 104 include, but are not limited to, sodium hypochlorite, methanol, iodine, hydrogen peroxide, alcohol, or chlorhexidine, In an embodiment, the auxiliary unit 114 is configured to emit at least one of the one or more protectants 118 to substantially sterilize the one or more contaminants 152. In such an embodiment, the auxiliary unit 114 can be configured to emit at least one of a disinfectant or an oxidizer. Examples of the one or more protectants 118 that can substantially sterilize at least one of the one or more contaminants 152 include, but are not limited to, heat, steam, hydrogen peroxide, such hydrogen peroxide gas plasma, or peroxygen. The phrase "substantially sterilize" includes the deactivation or destruction of at least 50% of the contaminants 152, at least 75% of the contaminants 152, at least 90% of the contaminants 152, or at least 95% to 99% of the contaminants 152 according to some embodiments.

In an embodiment, the auxiliary unit 114 is configured to emit at least one of the one or more protectants 118 to substantially intercept the one or more contaminants 152 prior to the one or more contaminants 152 contacting the nozzle portion 104. In an embodiment, the auxiliary unit 114 is configured to emit at least one of the one or more protectants 118 to substantially disperse the one or more contaminants 152 away from the nozzle portion 104. In an embodiment, the auxiliary unit 114 can be configured to emit at least one of the one or more protectants 118 to substantially deflect the one or more contaminants 152 away from the nozzle portion 104. For example, in such an embodiment, the auxiliary unit 114 is configured to emit at least one of the one or more protectants 118 in a first direction and the needleless injector unit 102 is configured to emit at least one of the one or more substances in a second direction. In an embodiment, the first direction and the second direction are related to one another such that they can be substantially parallel, substantially oblique, substantially orthogonal, or at any acute angle from 0 degrees to 90 degrees. In an embodiment, the first direction is substantially oblique to the skin surface 106 of the subject. In an embodiment, the first direction is substantially parallel to the skin surface 106 of the subject. In an embodiment, the first direction is substantially perpendicular to the skin surface 106 of the subject. In an embodiment, the second direction is substantially perpendicular to the skin surface 106 of the subject. In an embodiment, the second direction is substantially oblique to the skin surface 106 of the subject. In an embodiment, the auxiliary unit 114 is configured to emit at least one of the one or more protectants 118 to irradiate and substantially sterilize the one or more contaminants 152. For example, the auxiliary unit 114 is configured to emit at least ultraviolet electromagnetic radiation or infrared electromagnetic radiation.

In an embodiment, the auxiliary unit 114 is configured to emit at least one of the one or more protectants 118 at least partially based on one or more characteristics of the one or more contaminants 152. For example, the auxiliary unit 114 is configured to emit at least one of the one or more protectants 118 responsive to feedback from one or more sensors or detectors (see FIG. 2) that detects one or more characteristics of the one or more contaminants 152. For example, the one or more characteristics of the one or more contaminants 152 can include chemical characteristics thereof, physical characteristics thereof, density thereof, speed thereof, volume thereof, direction thereof, location thereof, or another suitable characteristic.

In an embodiment, the auxiliary unit 114 is configured to emit at least one of the one or more protectants 118 in one or more timed intervals. For example, the time intervals include, but are limited to, fixed time intervals, periodic time intervals, programmable or programmed time intervals, triggered time intervals, manually determined time intervals, automatic time intervals, remotely-controlled time intervals, or time intervals based on readouts from one or more sensors or detectors (see FIG. 2), as well as other appropriate time intervals. In an embodiment, the auxiliary unit 114 is configured to emit the one or more protectants 118 sequentially or separately. In an embodiment, the auxiliary unit 114 is configured to sequentially release a first one of the one or more protectants 118 followed by a second one of the one or more protectants 118. In an embodiment, the auxiliary unit 114 is configured to emit at least one of the one or more protectants 118 in one or more waves. For example, the auxiliary unit 114 is configured to emit a first one of the one or more protectants 118 and, before the auxiliary unit 114 stops emitting the first one of the one or more protectants 118, the auxiliary unit 114 can emit a second one of the one or more protectants 118. The auxiliary unit 114 can further be configured to stop emitting the first one of the one or more protectants 118 and to emit a third one of the one or more protectants 118. In an embodiment, the auxiliary unit 114 is configured to emit the one or more protectants 118 substantially during a first time period during which the one or more contaminants 152 are present in the vicinity of the nozzle portion 104. In an embodiment, the auxiliary unit 114 is configured to emit the one or more protectants 118 such that at least one of the one or more protectants 118 arrives at the skin surface 106 or the target region 124 before the one or more substances 110 arrive at the target region 124 of the skin surface 106. In an embodiment, the auxiliary unit 114 is configured to emit the one or more protectants 118, such that at least one of the one or more protectants 118 arrives at the skin surface 106 after the one or more substances 110 arrive at the skin surface 106 or the target region 124.

The needleless injector system 100 further includes a control unit 120 including control electrical circuitry (not shown), along with a user interface 122 (e.g., a touchscreen, keypad, etc.) for user input. The control unit 120 is operably coupled to the needleless injector unit 102 and the auxiliary unit 114 to control operation of one or more of the foregoing system components. For example, in operation, the nozzle portion 104 of the needleless injector unit 102 is positioned at least proximate to (e.g., near or adjacent to) a target region 124 on the skin surface 106. One or more injection-information signals 126 are output from the needleless injector unit 102 to the control unit 120 that encode injection information. In an embodiment, automatically responsive to the one or more injection-information signals 126, the control unit 120 outputs one or more protectant emitting instructions 128 to the auxiliary unit 114 without human intervention (e.g., without input from a user). In an embodiment, automatically and without human intervention, the auxiliary unit 114 may emit the one or more protectants 118 in accordance with the one or more protectant emitting instructions 128.

In an embodiment, the control unit 120 can output one or more injection-information signals 126 to the needleless injector unit 102 that encode injection information or directions. Responsive to the one or more injection-information signals 126, the needleless injector unit 102 can inject at least one of the one or more substances 110 from the nozzle portion 104 and transdermally through the skin surface 106. The control unit 120 can also output one or more protectant emitting instructions 128 to the auxiliary unit 114. In an embodiment, automatically and without human intervention, the auxiliary unit 114 emits the one or more protectants 118 in accordance with the protectant emitting instructions 128 to protect at least the nozzle portion 104 of the needleless injector unit 102. Thus, in an embodiment, the control unit 120 is configured to control operation of both the needleless injector unit 102 and the auxiliary unit 114.

In an embodiment, the injection information includes information that the needleless injector unit 102 has injected the one or more substances 110. In an embodiment, the injection information includes information that the needleless injector unit 102 is going to inject the one or more substances 110. In an embodiment, the injection information includes information that the needleless injector unit 102 is injecting the one or more substances 110 from the nozzle portion 104. In an embodiment, the injection information includes information about one or more characteristics of the one or more substances 110. In an embodiment, the injection information includes information about one or more characteristics of the one or more contaminants 152.

In an embodiment, the one or more protectant emitting instructions 128 include one or more directions to emit at least one of the one or more protectants 118 prior to the needleless injector unit 102 injecting the one or more substances 110. In an embodiment, the one or more protectant emitting instructions 128 include one or more directions to emit at least one of the one or more protectants 118 after the needleless injector unit 102 injects the one or more substances 110. In an embodiment, the one or more protectant emitting instructions 128 include one or more directions to emit at least one of the one or more protectants 118 substantially simultaneously with the needleless injector unit 102 injecting the one or more substances 110. In an embodiment, the one or more protectant instructions 128 include one or more directions to emit at least one of the one or more protectants responsive to the needleless injector unit 102 injecting the one or more substances 110. In an embodiment, the one or more protectant emitting instructions 128 include one or more directions to emit the one or more protectants 118 prior to and after the needleless injector unit 102 injects the one or more substances 110. In an embodiment, the one or more protectant emitting instructions 128 include one or more directions to emit the one or more protectants 118 after the needleless injector unit 102 injects the one or more substances 110 to seal the nozzle portion 104. In an embodiment, the one or more protectant emitting instructions 128 include one or more directions to emit at least one of the one or more protectants 118 based on one or more characteristics of the one or more substances 110. In an embodiment, the one or more protectant emitting instructions 128 include one or more directions to emit at least one of the one or more protectants 118 based on one or more characteristics of the one or more contaminants 152. In an embodiment, the one or more protectant emitting instructions 128 include one or more directions to emit at least one of the one or more protectants in one or more timed intervals. In an embodiment, the one or more protectant emitting instructions 128 include one or more directions to emit at least one or more protectants in one or more waves.

In an embodiment, the control unit 120 is configured (e.g., programmed) with a plurality of different settings that are user selectable via the user interface 122. In such an embodiment, the auxiliary unit 114 emits at least one of the one or more protectants 118 corresponding to a selected one of the plurality of different settings selected via the user interface 122. It should be noted that the any of the instructions herein can be implemented via software, firmware, or hardware in the control electrical circuitry of the control unit 120 or associated components.

Figure 1B:
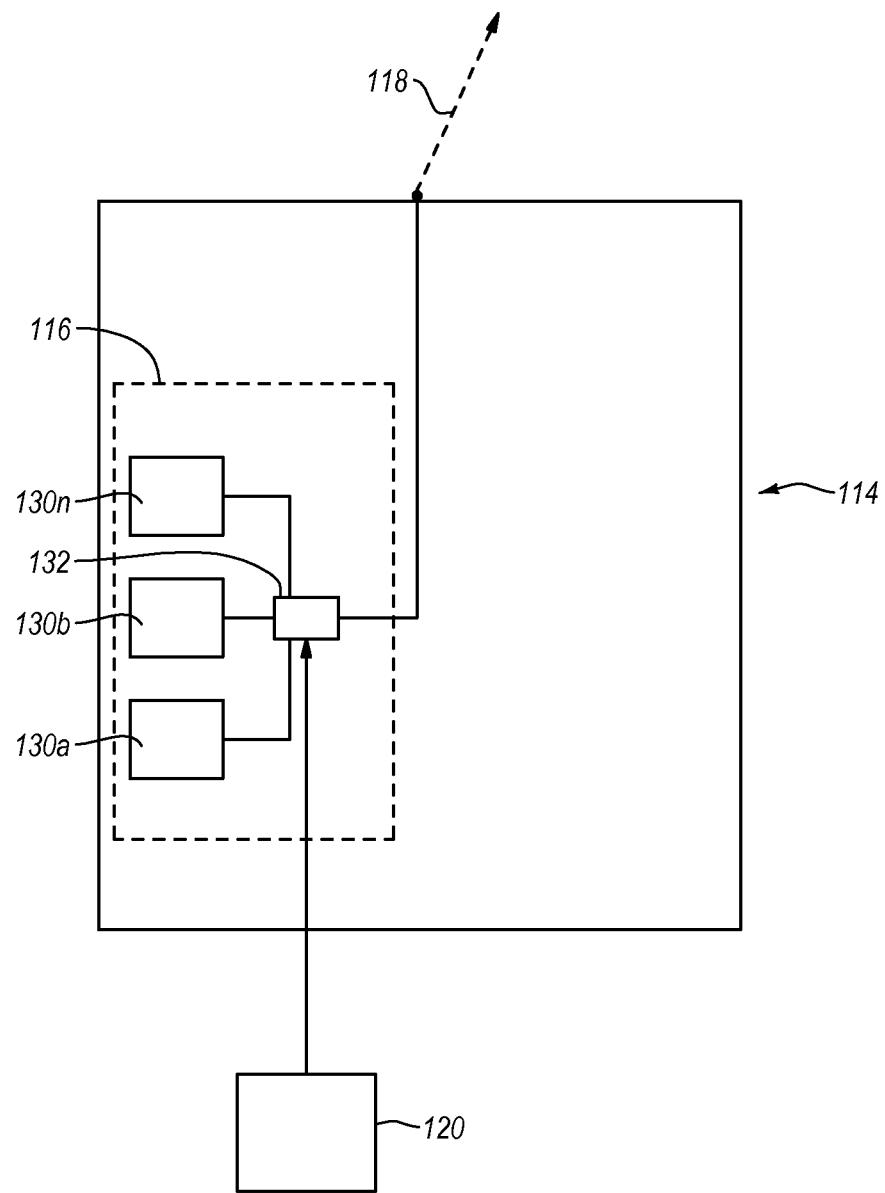
FIG. 1B is a schematic diagram of an embodiment of an auxiliary unit including multiple containers and a corresponding fluid dispensing unit.

Referring to FIG. 1B, in an embodiment, the source 116 of the one or more protectants includes a plurality of containers $130_a$-$130_n$ that hold different protectants 118 to be emitted by the auxiliary unit 114 via a dispensing unit 132. In an embodiment, at least one of the one or more protectants 118 can include a gas, a liquid, or a solid phase of a material. For example, at least one of the one or more protectants 118 includes any of the protectants disclosed herein, such as at least one of a disinfectant, an oxidizer, an acid, a base, cleaning fluid, an adhesive, a neutralizer, air, or water. In an embodiment, at least one of the one or more protectants 118 substantially entraps or entrains the one or more contaminants 152. In an embodiment, at least one of the one or more protectants 118 substantially neutralizes the one or more contaminants 152. In an embodiment, at least one of the one or more protectants 118 forms a semi-permeable barrier or membrane. For example, at least one of the one or more protectants 118 forms a barrier over the target region 124 (see FIG. 1A) that allows the one or more therapeutic materials to pass through but not the one or more contaminants 152. An example, of a suitable barrier includes a barrier layer of the one or more protectants 118 coating the skin surface 106 of the subject. In an embodiment, at least one of the one or more protectants 118 forms a barrier over the target region 124 that only allows therapeutic materials traveling from one or more directions toward the target region 124 to pass through the barrier formed by the at least one of the one or more protectants 118. In an embodiment, at least one of the one or more protectants 118 at least partially disinfects or cleans the nozzle portion 104 of the needleless injector unit 102. In an embodiment, at least one of the one or more protectants seals the target region 124 after injection of the one or more substances 110. In an embodiment, at least one of the one or more protectants caps the target region 124 after injection of the one or more substances 110.

In an embodiment, the dispensing unit 132 can include at least one of a fluid dispensing unit, a force generating mechanism, an actuator, a piston, a pump (e.g., a mechanical pump, or an electro-mechanical pump), or another suitable dispensing unit. For example, the dispensing unit 132 can include at least one of a pneumatic actuator, a hydraulic actuator, a piezoelectric actuator, a linear actuator, an electro-mechanical actuator, or another suitable actuator. The dispensing unit 132 is configured to selectively dispense the one or more protectants 118 from the containers $130_a$-$130_n$. The dispensing unit 132 is configured to selectively emit the one or more protectants 118 from the auxiliary unit 114. The containers $130_a$-$130_n$ can be individually operably coupled to the dispensing unit 132 via conduits and corresponding electronically controlled valves (not shown) that can be selectively opened and closed via one or more control signals from the control unit 120 to allow the one or more protectants 118 to be selectively dispensed by the dispensing unit 132 from the containers $130_a$-$130_n$. For example, one or more of the containers $130_a$-$130_n$ can hold adhesives, while one or more of the containers $130_a$-$130_n$ can hold disinfectants.

In operation, the nozzle portion 104 of the needleless injector unit 102 is positioned at least proximate to a target region 124 on the skin surface 106. In an embodiment, prior to, substantially simultaneously with, or after the needleless injector unit 102 injects the one or more substances 110 from the nozzle portion 104, a protectant 118 is selectively dispensed from a corresponding one of the containers $130_a$-$130_n$ using the dispensing unit 132 (under control of the control unit 120) and emitted by the dispensing unit 132 out of the auxiliary unit 114.

Figure 1C:
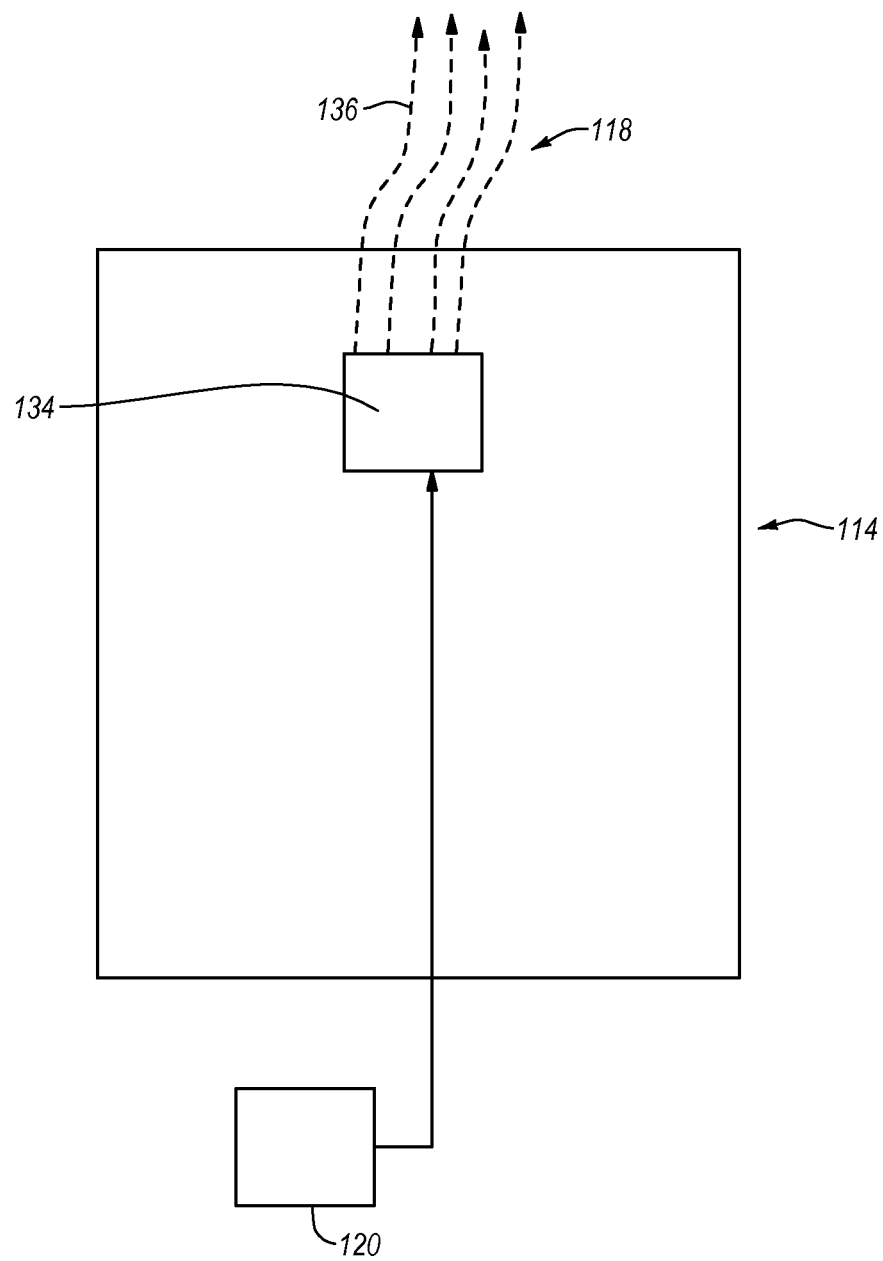
FIG. 1C is a schematic diagram of an embodiment of an auxiliary unit including a radiation source.

Referring to FIG. 1C, in an embodiment, the source of protectants 118 of the auxiliary unit 114 includes one or more electromagnetic (EM) radiation sources 134 configured to output EM radiation 136 as a protectant 118 by the auxiliary unit 114. For example, the one or more EM radiation sources 134 can include a light emitting diode, a laser, a semiconductor laser, or other suitable radiation emitting device. In an embodiment, the EM radiation 136 includes light radiation. For example, light radiation can include EM radiation within at least one of the spectrum of ultraviolet (UV) EM radiation, visible light, infrared (IR) EM radiation, terahertz EM radiation, microwave EM radiation, or radio wave EM radiation. For example, the EM radiation 136 can be chosen to substantially sterilize the one or more contaminants 152. As another example, the EM radiation 136 can include at least one of an acoustic radiation such as ultrasonic radiation. For example, radio wave radiation may include, for example, at least one of ultra-high frequency radio waves (UHF), very high frequency radio waves (VHF), radio frequency (RF), or extremely low frequency (ELF) radio waves. In an embodiment, the EM radiation 136 includes a non-ionizing radiation. The one or more EM radiation sources 134 can be selectively activated and de-activated via one or more control signals from the control unit 120 to allow the EM radiation 136 to be selectively emitted from the one or more radiation sources 134. In an embodiment, the EM radiation 136 is output by at least one of the one or more EM radiation sources 134 in one or more microsecond duration pulses.

In operation, the nozzle portion 104 (shown in FIG. 1A) of the needleless injector unit 102 is positioned at least proximate to the target region 124 on the skin surface 106. In an embodiment, prior to, substantially simultaneously with, or after the needleless injector unit 102 injects the one or more substances 110 from the nozzle portion 104, the EM radiation 136 is selectively emitted using the one or more radiation sources 134 (under control of the control electrical circuitry of control unit 120) out of the auxiliary unit 114 to protect at least the nozzle portion 104 of the needleless injector unit 102.

Figure 1D:
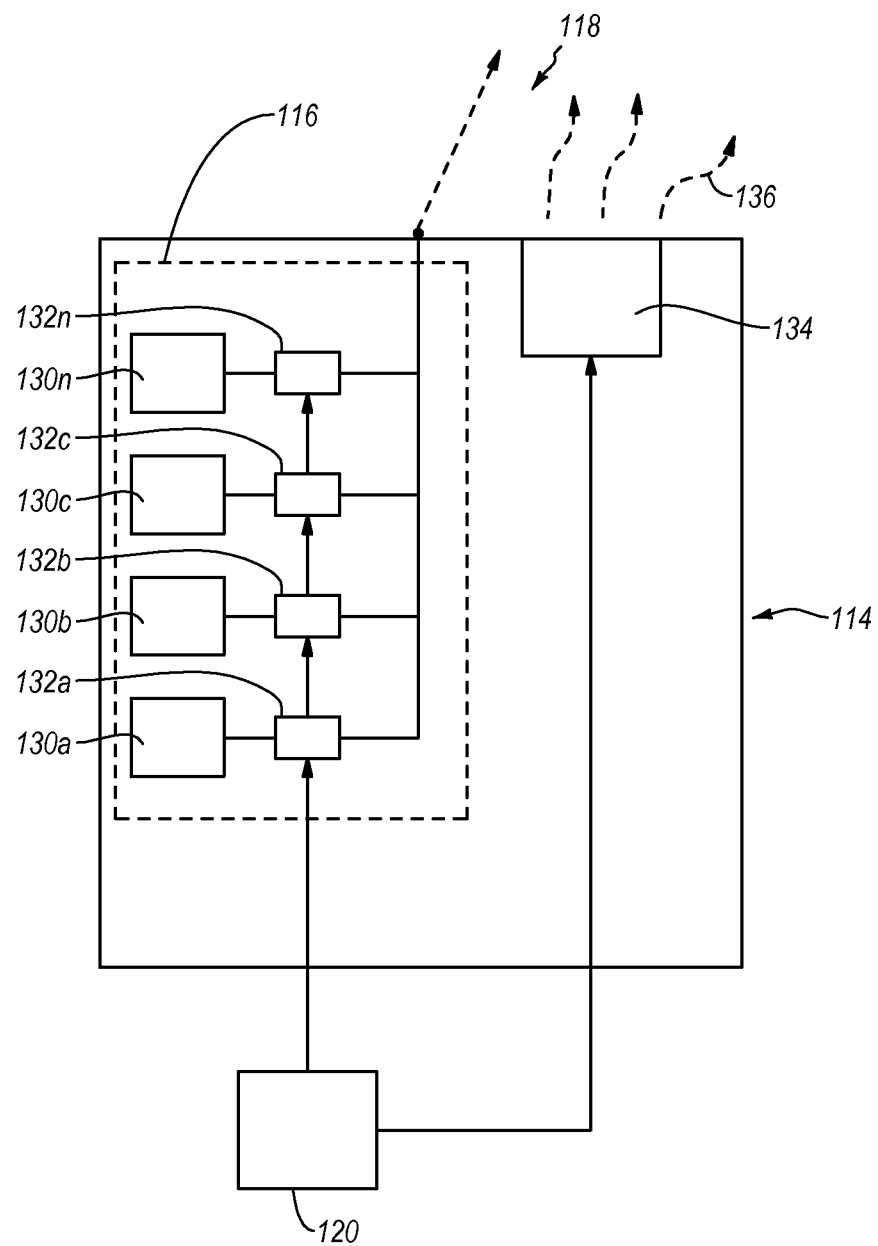
FIG. 1D is a schematic diagram of an embodiment of an auxiliary unit including multiple containers and corresponding fluid dispensing units and a radiation source.

Referring to FIG. 1D, in an embodiment, the auxiliary unit 114 includes a source 116 having a plurality of containers $130_a$-$130_n$ that hold different protectants 118 to be emitted by the auxiliary unit 114 via one or more dispensing units $132_a$-$132_n$ to a region between the nozzle portion 104 of the needleless injector unit 102 and the skin surface 106. For example, the one or more of the dispensing units $132_a$-$132_n$ can include a piston, a fluid dispensing unit, an actuator, a pump (e.g., a mechanical pump, an electro-mechanical pump), or another suitable dispensing unit. For example, one or more of the dispensing units $132_a$-$132_n$ can include a pneumatic actuator, a hydraulic actuator, a piezoelectric actuator, a linear actuator, an electro-mechanical actuator, or another suitable actuator. In an embodiment, the dispensing units $132_a$-$132_n$ selectively dispense the one or more protectants 118 from the containers $130_a$-$130_n$. In an embodiment, the dispensing units $132_a$-$132_n$ selectively emit the one or more protectants 118 from the auxiliary unit 114. The containers $130_a$-$130_n$ can be individually operably coupled to the corresponding dispensing units $132_a$-$132_n$ via conduits and corresponding electronically controlled valves (not shown) that can be selectively opened and closed via one or more control signals from the control unit 120 to allow the one or more protectants 118 to be selectively dispensed from the containers $130_a$-$130_n$.

The auxiliary unit 114 also includes one or more EM radiation sources 134 configured to output EM radiation 136 as a protectant 118 by the auxiliary unit 114. In an embodiment, the EM radiation 136 can include electromagnetic radiation, such as ultraviolet radiation, infrared radiation, ultrasonic radiation, or any other type of sterilizing energy. The one or more radiation sources 134 is selectively activated and de-activated via one or more control signals from the control unit 120 to allow the radiation 136 to be selectively emitted from the one or more radiation sources 134.

In operation, the nozzle portion 104 (shown in FIG. 1A) of the needleless injector unit 102 is positioned at least proximate to a target region 124 on the skin surface 106. Prior to, substantially simultaneously with, or after the needleless injector unit 102 injects the one or more substances 110 from the nozzle portion 104, a protectant 118 is selectively dispensed from a corresponding one of the containers $130_a$-$130_n$ using a corresponding one of the dispensing units $132_a$-$132_n$ (under control of the control unit 120) and emitted out of the auxiliary unit 114 or a protectant 118 including EM radiation 136 is selectively emitted using the one or more radiation sources 134 (under control of the control unit 120) out of the auxiliary unit 114 to a region between the nozzle portion 104 and the skin surface 106. In an embodiment, the emitted protectant(s) 118 protects at least the nozzle portion 104 of the needleless injector unit 102.

Figure 2:
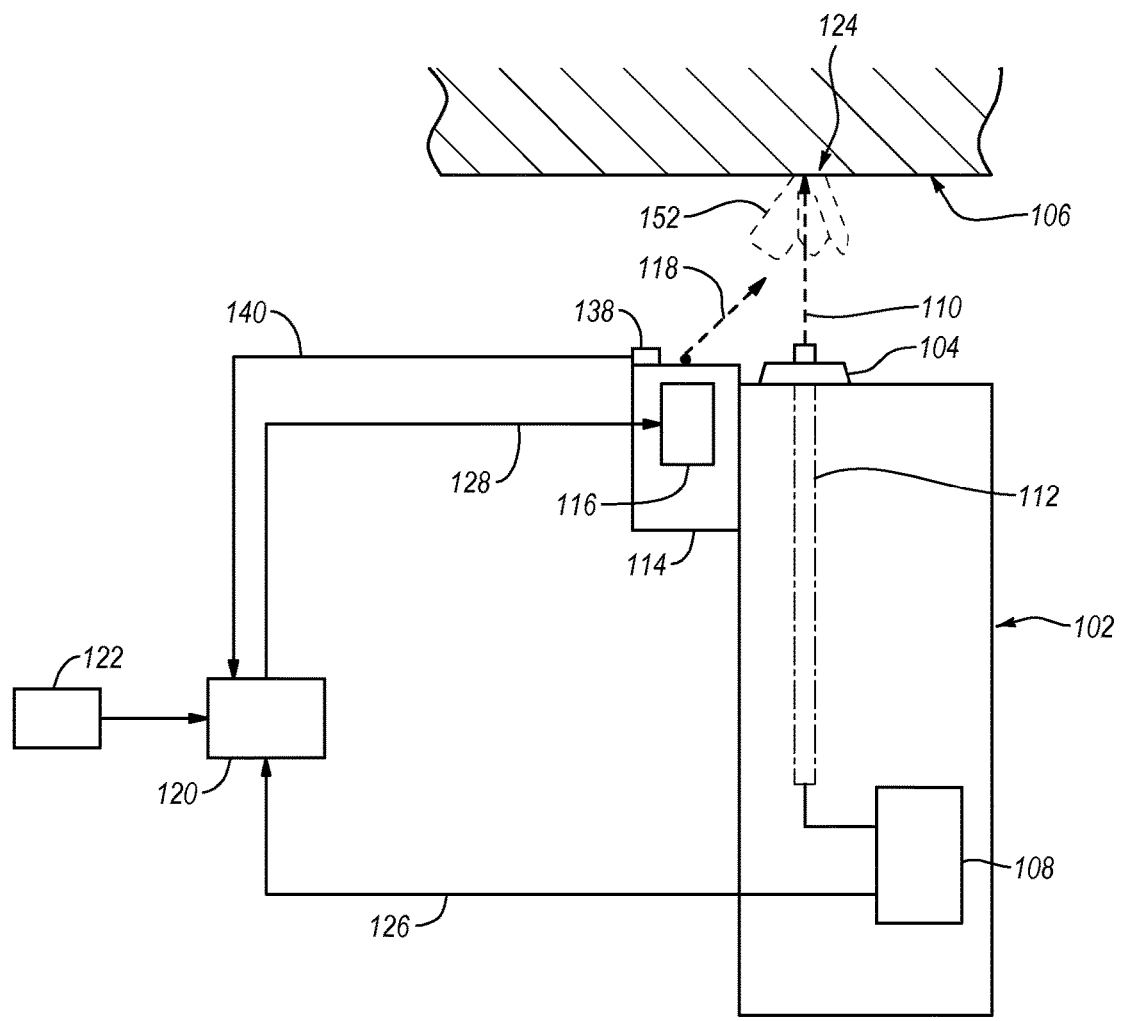
FIG. 2 is a schematic diagram of an embodiment of a needleless injector system including an auxiliary unit selectively emitting one or more protectants.

In any of the disclosed needleless injector systems embodiments, a needleless injector system can include one or more sensors operably associated with an auxiliary unit to sense one or more parameters. For example, referring to the embodiment shown in FIG. 2, one or more sensors 138 are operably associated with the auxiliary unit 114 of the needleless injector system 100 of FIG. 1A. In the illustrated embodiment, the one or more sensors 138 are coupled (e.g., mounted) to the auxiliary unit 114. However, in another embodiment, the one or more sensors 138 are coupled to the needleless injector unit 102. In an embodiment, the one or more sensors 138 are physically coupled to the skin surface 106.

The one or more sensors 138 can include, but are not limited to ultrasound sensors, pressure sensors, light sensors, sensors including piezoelectric crystals, encoders, transducers, motion sensors, position sensors, flows sensors, viscosity sensors, shear sensors, time detectors (e.g., timer, clocks), imaging detectors, acoustic sensors, temperature sensors, chemical and biological detectors, electromagnetic energy detectors (e.g., optical energy such as near IR, UV, visual), pH detectors, or electrical sensors. The one or more sensors 138 can be configured to measure various characteristics of the one or more or contaminants 152, the nozzle portion 104, the target region 124, or the one or more substances 108, such characteristics including, but not limited to, electrical resistivity thereof, presence thereof, position, spray pattern thereof, speed thereof, direction thereof, chemical composition thereof, pH thereof, or density thereof. One or more of these or other sensing capabilities can be present in a single sensor or an array of sensors; sensing capabilities are not limited to a particular number or type of sensors.

The one or more sensors 138 can be small in size, such as a sensor or a sensor array that is a chemical sensor, a gas sensor, or a biosensor. One or more sensors 138 including one or more electromagnetic energy detectors can be configured to measure the absorption, emission, fluorescence, or phosphorescence of one or more targets. Such electromagnetic properties can be inherent properties of all or a portion of one or more targets, or can be associated with materials added or introduced to the targets, such as tags or markers for one or more targets. One or more targets may include, but are not limited to, at least a portion of the target region 124, the one or more contaminants 152, the one or more substances 108, or the nozzle portion 104.

The one or more sensors 138 including one or more spectroscopy sensors, biosensors, or chemical sensors can detect a composition or materials including, but not limited to, a pathogen, a protein, a nucleic acid, a cell, an organic compound, a drug, an acid, an alcohol, a pollutant, a contaminant, or a tag. One or more sensors 138 including a machine-vision system can detect location, quality of location, or quality of injection placement of the one or more substances 108 or the target region 124. The machine-vision system may include, but is not limited to, at least one of ultrasound imaging system, a thermal imaging system, an electronic camera, or visual imaging. In an embodiment, one or more sensors 138 including a contactless infrared sensor or optical coherency tomography sensor can detect one or more physiological conditions of a subject, including, but not limited to, tissue swelling, inflammation, and temperature.

In an embodiment, the one or more sensors 138 includes an array of pressure sensors that detect strain (or deflection) due to pressure over an area in the region between the nozzle portion 104 and the skin surface 106 to facilitate the determination of location, speed, velocity, or spatial information (e.g., direction, spray pattern, or presence) of one or more targets. The one or sensors 138 convert pressure energy to one or more sensing signals 140 in the form of electrical energy. In an embodiment, one or more analog-to-digital converters (ADC) convert the electrical energy to digital data that is provided to the control unit 120. The ADC can be a separate component, can be integrated into the control unit 120, or can be integrated into the one or more sensors 138. In an embodiment, the control unit 120 includes processing hardware (e.g., processing electrical circuitry) and an operating system configured to run one or more application software programs. The control unit 120 can use one or more processing techniques to analyze the digital data in order to determine different parameters, including, but not limited, location, speed, velocity, direction, spray pattern, or presence of the of the one or more targets (e.g., at least a portion of the target region 124, the one or more contaminants 152, the one or more substances 108, or the nozzle portion 104).

In an embodiment, the one or more sensors 138 include one or more transceivers that generate one or more signals within one or more frequency bands for monitoring the region between the nozzle portion 104 and the skin surface 106 to facilitate the determination of location, speed, direction, spray pattern, presence of one or more targets. One or more targets can include, but are not limited to, at least a portion of the target region 124, the one or more contaminants 152, the one or more substances 108, the one or more protectants 110, or the nozzle portion 104. The one or more sensors 138 receive responses (e.g., reflection of the one or more signals, absorption of the one or more signals, refraction of the one or more signals, pass through of the one or more signals, angle of incident of the one or more signals, backscattering of the one or more signals, a response to the one or more signals to produce measured signal effects), convert the responses to one or more sensing signals 140, and provide the one or more sensing signals 140 to the control unit 120. In an embodiment, the control unit 120 includes processing hardware (e.g., processing electrical circuitry) and an operating system configured to run one or more application software programs. The control unit 120 uses one or more processing techniques on the one or more sensing signals 140 to determine at least location, speed, velocity, direction, spray pattern, or presence of the of the one or more targets (e.g., at least a portion of the target region 124, the one or more contaminants 152, the one or more substances 108, or the nozzle portion 104). For example, analysis of the one or more sensing signals 140 can generate the distance to the one or more sensors 138. From the distance for a plurality of sensing signals 140, the spatial information (e.g., position, spray pattern, presence) of the one or more targets can be determined by the control unit 120. In addition to determining spatial information, the control unit 120 can determine motion information (e.g., speed, velocity, direction) for the one or more targets based on the one or more sensing signals 140 received from the one or more sensors 138. For example, signals generated by the transceiver (e.g., the one or more signals within the one or more frequency bands for monitoring the region) can be spaced between about 100 nanoseconds and 100 microseconds apart to allow the control unit 120 to determine motion information (e.g., direction, velocity, speed, movement) of the one or more targets. The signals can be emitted with non-uniform spacing such as random or pseudo-random spacing, although constant spacing can be used in interference or compliance is not a concern. Spacing between the signals can be varied responsive to detection of the one or more targets. For example, the spacing between the signals can be relatively large when a target (e.g., a substance 110) is not detected in the region between the nozzle portion 104 and the skin surface 106. Spacing between the signals can be decreased (responsive to one or more commands from the controller unit 120) when a target is detected in the region.

In an embodiment, the one or more sensors 138 include an ultrasound transceiver that transmits one or more ultrasound signals within an ultrasound frequency band. The ultrasound transceiver receives at least one inbound ultrasound signal (e.g., reflection, refraction, echo, etc.) that facilitates the measuring of the at least one of the reflection of the one or more signals, the absorption of the one or more signals, refraction of the one or more signals, the pass through of the one or more signals, the angle of incident of the one or more signals, or the backscattering of the one or more signals to produce measured signal effects.

In an embodiment, the one or more sensors 138 include a radio frequency (RF) transceiver that transmits one or more signals within a radio frequency band. The RF transceiver receives at least one inbound RF signal (e.g., reflection, refraction, response, backscatter, etc.) that facilitates the measuring of the at least one of the reflection of the one or more signals, the absorption of the one or more signals, refraction of the one or more signals, the pass through of the one or more signals, the angle of incident of the one or more signals, or the backscattering of the one or more signals to produce measured signal effects.

In an embodiment, the one or more sensors 138 include a microwave transceiver that transmits the one or more signals within a microwave frequency band. The microwave transceiver receives at least one inbound microwave signal (e.g., reflection, refraction, response, backscatter, etc.) that facilitates the measuring of the at least one of the reflection of the one or more signals, the absorption of the one or more signals, refraction of the one or more signals, the pass through of the one or more signals, the angle of incident of the one or more signals, or the backscattering of the one or more signals to produce measured signal effects.

In an embodiment, the one or more sensors 138 include an infrared transceiver that transmits the one or more signals within an infrared frequency band. The infrared transceiver receives at least one inbound infrared signal (e.g., reflection, refraction, angle of incidence, response, backscatter, etc.) that facilitates the measuring of the at least one of the reflection of the one or more signals, the absorption of the one or more signals, refraction of the one or more signals, the pass through of the one or more signals, the angle of incident of the one or more signals, or the backscattering of the one or more signals to produce measured signal effects.

In an embodiment, the one or more sensors 138 include a laser transceiver that transmits the one or more signals within a visible light frequency band. The laser transceiver, which may use fiber optics, receives at least one inbound visible light signal (e.g., reflection, refraction, response, backscatter, etc.) that facilitates the measuring of the at least one of the reflection of the one or more signals, the absorption of the one or more signals, refraction of the one or more signals, the pass through of the one or more signals, the angle of incident of the one or more signals, or the backscattering of the one or more signals to produce measured signal effects.

In an embodiment, the one or more sensors 138 include an ultraviolet transceiver that transmits the one or more signals within an ultraviolet radiation frequency band. The ultraviolet transceiver receives at least one inbound ultraviolet radiation signal (e.g., reflection, absorption, or refraction of UV light off the nozzle portion 104, the contaminant 152, and the substance 110) that facilitates the measuring of the at least one of the reflection of the one or more signals, the absorption of the one or more signals, refraction of the one or more signals, the pass through of the one or more signals, the angle of incident of the one or more signals, or the backscattering of the one or more signals to produce measured signal effects.

In an embodiment, the one or more sensors 138 includes one or more of the ultrasound transceiver, the RF transceiver, the microwave transceiver, the infrared transceiver, the laser transceiver, or the ultraviolet transceiver. As noted above, the control unit 120 can receive the one or more sensing signals 140 from the one or more sensors 138 and process them to determine one or more characteristics of the one or more targets (e.g., at least a portion of the target region 124, the one or more contaminants 152, the one or more substances 108, or the nozzle portion 104) including, but not limited to, location, speed, direction, spray pattern, or presence.

In an embodiment, the one or more sensors 138 includes a position sensor (e.g., a micropower impulse radar sensor) operably associated with the auxiliary unit 114 that senses a position of the nozzle portion 104 relative to the target region 124 or the one or more contaminants 152. The control unit 120 is configured to control direction or placement of the one or more protectants 118 emitted from the auxiliary unit 114 responsive to the one or more sensing signals from the one or more sensors 138 encoding a position of the nozzle portion 104.

As described above, the one or more sensors 138 can output one or more sensing signals 140 responsive to sensing different parameters or characteristics. The control unit 120 can receive the one or more sensing signals 140 from the one or more sensors 138. In an embodiment, the control unit 120 includes processing hardware (e.g., processing electrical circuitry) and an operating system configured to run one or more application software programs. The control unit 120 can use one or more processing techniques implemented on the one or more application software programs to determine one or more characteristics from the one or more sensing signals 140. In an embodiment, the one or more processing techniques include the control unit 120 communicating with a database to compare the one or more sensing signals 140 with one or more possible datasets to correlate the one or more sensing signals 140 with certain known one or more characteristics about the one or more protectants 118 or the contaminants 152. In an embodiment, the one or more processing techniques include the control unit 120 interpreting, filtering, or conditioning the one or more sensing signals 140. In an embodiment, the one or more processing techniques include the control unit 120 transforming the one or more sensing signals. In an embodiment, the one or more processing techniques include the control unit 120 using one or more algorithms to yield information from the one or more sensing signals 140.

In an embodiment, the control unit 120 (including the control electrical circuitry) is configured to direct the auxiliary unit 114 to emit one or more of the one or more protectants 118 responsive to the one or more sensing signals 140 output by the one or more sensors 138. In an embodiment, the control unit 120 is configured to send one or more activation signals to the auxiliary unit 114 that include directions to emit at least one of the one or more protectants 118. In an embodiment, the control unit 120 is configured to direct the auxiliary unit 114 to emit at least one of the one or more protectants 118 in one or more different directions responsive to the one or more sensing signals 140 output by the one or more sensors 138. In an embodiment, the control unit 120 is configured to direct the auxiliary unit 114 to stop emitting at least one of the one or more protectants 118 responsive to the one or more sensing signals 140 output by the one or more sensors 138. In an embodiment, the one or more sensors 138 is configured to measure one or more distances between the nozzle portion 104 and the skin surface 106 of the subject. In such an embodiment, the control unit 120 is configured to direct the auxiliary unit 114 to emit at least one of the one or more protectants 118 responsive to at least the one or more distances measured and received from the one or more sensors 138.

Figure 3:
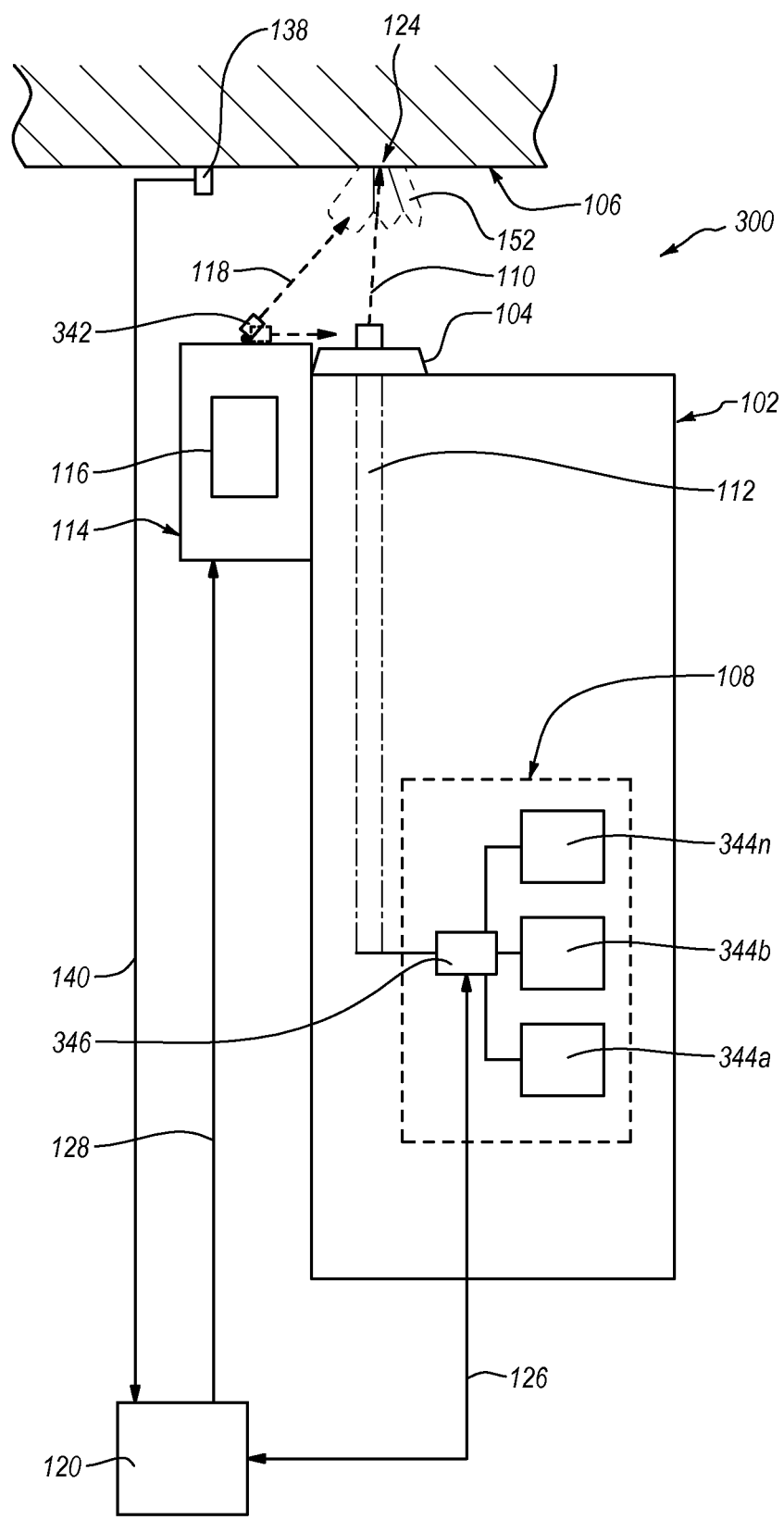
FIG. 3 is a schematic diagram of an embodiment of a needleless injector system that includes one or more sensors coupled to a control unit.

FIG. 3 is a schematic diagram of an embodiment of a needleless injector system 300 including an auxiliary unit having an articulating nozzle portion. The needleless injector system 300 includes many of the same components as the needleless injector system 100 shown in FIGS. 1A and 2. Therefore, in the interest of brevity, components of the needleless injector systems 100 and 300 that are identical or similar to each other have been provided with the same reference numerals, and an explanation of their structure and function will not be repeated unless the components function differently in the needleless injector systems 100 and 300. However, it should be noted that the principles of the needleless injector system 300 are employed with any of the embodiments described with respect to FIGS. 1A through 2.

The needleless injection system 300 may include an auxiliary unit 114 including an articulating nozzle portion 342 positionable at or near the skin surface 106 of the subject. The auxiliary unit 114 may also include a source 116 of one or more protectants 118. The auxiliary unit 114 is configured to emit at least one of the one or more protectants 118 from the articulating nozzle portion 342 to a region between the nozzle portion 104 and the skin surface 106. In an embodiment, the auxiliary unit 114 is configured to emit at least one of the one or more protectants 118 from the articulating nozzle portion 342 to protect at least the nozzle portion 104 of the needleless injector unit 102. In an embodiment, one or more sensors 138 is operably associated with the auxiliary unit 114 of the needleless injector system 300. In the illustrated embodiment, the one or more sensors 138 is coupled to the skin surface 106. In an embodiment, the one or more sensors 138 is configured to sense any of the aforementioned one or more parameters or characteristics detectable by the one or more sensors 138 shown in FIG. 2.

The one or more sensors 138 may output one or more sensing signals 140 responsive to sensing such parameters. In such an embodiment, the control unit 120 (including the control electrical circuitry) is configured to direct the auxiliary unit 114 to emit at least one of the one or more protectants 118 responsive to the one or more sensing signals 140 output by the one or more sensors 138. The control unit 120 is further operably coupled to and configured to direct the auxiliary unit 114 to move the articulating nozzle portion 342 responsive to the one or more sensing signals 140 output by the one or more sensors 138. For example, in an embodiment, the one or more sensors 138 is configured to detect the presence of one or more contaminants 152 traveling toward the nozzle portion 104 of the needleless injector unit 102. The one or more sensors 138 is configured to output the one or more sensing signals 140 containing information about the incoming one or more contaminants 152. Responsive to receiving the one or more sensing signals 140 from the one or more sensors 138, the control unit 120 is configured to direct the auxiliary unit 120 to move or aim the articulating nozzle portion 342 toward the incoming one or more contaminants 152 and to emit at least one of the one or more protectants 118. In an embodiment, responsive to receiving the one or more sensing signals 140 from the one or more sensors 138, the control unit 120 is configured to direct the auxiliary unit 120 to move or aim the articulating nozzle portion 342 toward the nozzle portion 104 and to emit at least one of the one or more protectants 118. In such an embodiment, the auxiliary unit 114 is configured to substantially disinfect or substantially clean the nozzle portion 104 of the needleless injector unit 102.

In an embodiment, the supply 108 may include a plurality of containers $\mathbf{344}_a$-$\mathbf{344}_n$ that hold different substances 110 to be injected from the nozzle portion 104 and through the skin surface 104 of the subject. In an embodiment, the substances 110 can include liquids, solutions, suspensions, mixtures, diluents, reagents, solvents, micro-particles, molecules, emulsions, saline solution, non-medical fluids, or any other fluids suitable for injection. In an embodiment, the substances 110 can include medicinal or therapeutic substances, such as, for example, but not limited to, at least one of antiseptics, vaccines, drugs, nucleotide based (e.g., DNA, RNA) medications, pharmaceutical vehicles or excipients, pain killers, coagulants, hormones, or antibiotics. The plurality of containers $\mathbf{344}_a$-$\mathbf{344}_n$ is operatively coupled to a dispensing unit 346 dispensing the one or more substances 110 through the passageway 112 and out the nozzle portion 104. In an embodiment, the containers $\mathbf{344}_a$-$\mathbf{344}_n$ are individually operably coupled to the dispensing unit 346 via conduits and corresponding electronically controlled valves (not shown) that are selectively opened and closed via one or more control signals from the control unit 120 to allow the one or more substances to be selectively dispensed from the containers $\mathbf{344}_a$-$\mathbf{344}_n$. In operation, the control unit 120 may direct the dispensing unit 346 to dispense a substance or drug from one of the containers $\mathbf{344}_a$-$\mathbf{344}_n$. Subsequently, the control unit 120 may direct the dispensing unit 346 to dispense coagulant from one of the containers $\mathbf{344}_a$-$\mathbf{344}_n$.

Figure 4A:
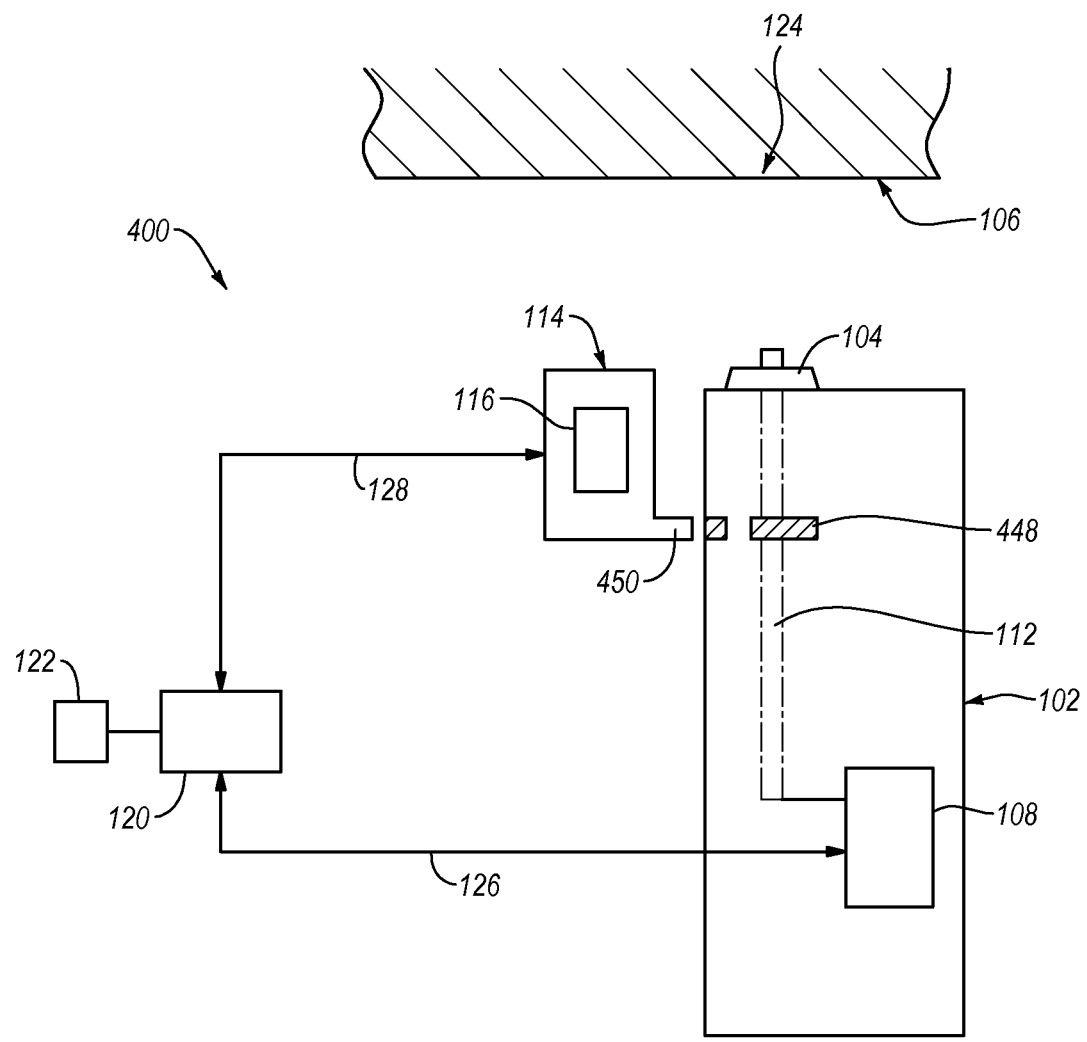
FIG. 4A is a schematic diagram of an embodiment of a needleless injector system including an interlock.
Figure 4B:
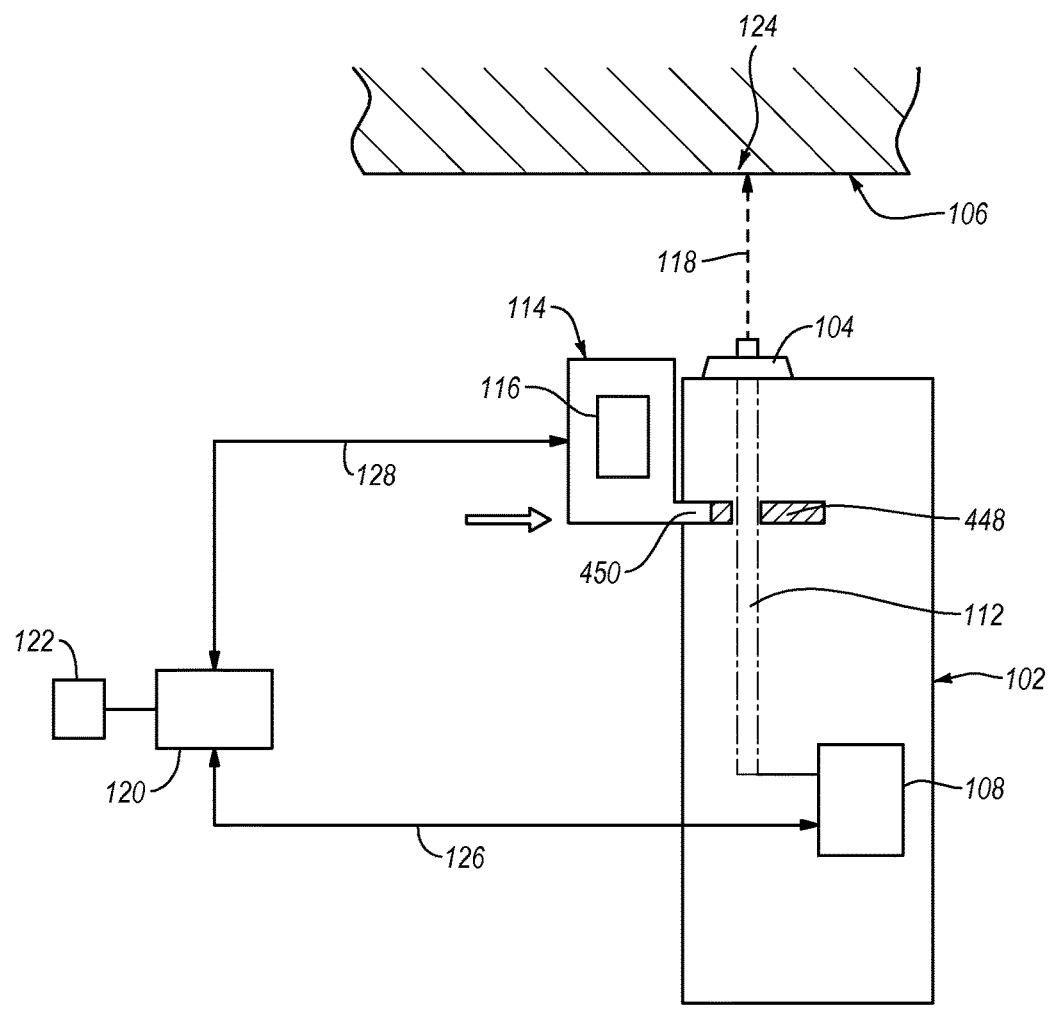
FIG. 4B is a schematic diagram of another embodiment of a needleless injector system including an interlock.
Figure 5:
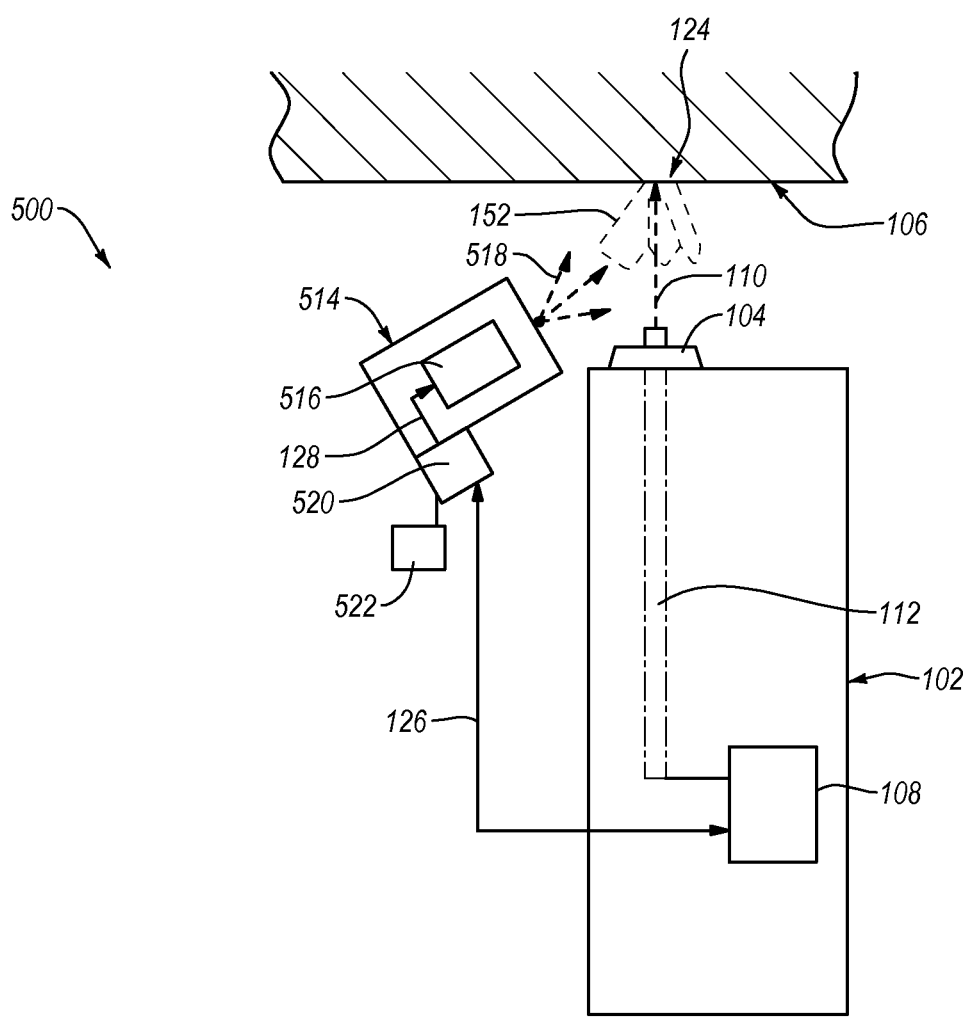
FIG. 5 is a schematic diagram of an embodiment of an auxiliary unit that is not physically coupled to a needleless injector system.

FIGS. 4A and 4B are schematic diagrams of an embodiment of a needleless injector system 400 including an auxiliary unit 114. The needleless injector system 400 includes many of the same components as the needleless injector systems 100 and 300 shown in FIGS. 1A and 3. Therefore, in the interest of brevity, components of the needleless injector systems 100, 300, and 400 that are identical or similar to each other have been provided with the same reference numerals, and an explanation of their structure and function will not be repeated unless the components function differently in the needleless injector systems 100, 300 and 400. However, it should be noted that the principles of the needleless injector system 400 are employed with any of the embodiments described with respect to FIGS. 1A through 3.

The needleless injector system 400 may include one or more interlocks 448 configured to prevent injection of the one or more substances 110 if the auxiliary unit 114 is not coupled to the needleless injector unit 102 or if the quantity of the one or more protectants 118 in the source 116 is below a specific level. For example, in an embodiment, the interlock 448 is positioned within the passageway 112 and moveable between a first position in which the interlock 448 prevents passage of the one or more substances 110 through the passageway 112, and a second position in which the interlock 448 allows passage of the one or more substances 110 through the passageway 122. In an embodiment, the auxiliary unit 114 may include an actuator 450 configured to move the interlock 448 between the first position and the second position. For example, as shown in FIG. 4A, in an embodiment, when the auxiliary unit 114 is uncoupled from the needleless injector unit 102, the interlock 448 is in the first position, in which the interlock 448 prevents passage of the one or more substances 110 through the passageway 112. As shown in FIG. 4B, when the interlock 448 is coupled to the needleless injector unit 102, the actuator 450 on the auxiliary unit 114 is configured to exert a force on the interlock 448 to move the interlock 448 toward the second position, in which the interlock 448 allows passage of the one or more substances 110 through the passageway 122 and out of the nozzle portion 104.

In an embodiment, the control unit 120 is operably coupled to the interlock 448 and the auxiliary unit 114 to control operation of the foregoing system components. For example, the auxiliary unit 114 may determine the quantity of the one or more protectants 118 in the source 116 and outputs one or more source-information signals encoding protectant quantity information to the control unit 120. Responsive, if the quantity of the one or more protectants 118 is below one or more pre-determined levels, the control unit 120 may direct the interlock 448 to move from the second position to the first position, in which the interlock 448 prevents passage of the one or more substances 110 through the passageway 112. In an embodiment, the control unit 120 can use software, firmware, or control electrical circuitry to operationally achieve interlock functionality by preventing the issuance of, or blocking the delivery of, injection-information signals 126 if the auxiliary unit 114 is not coupled to the needleless injector unit 102 or if the quantity of the one or more protectants 118 in the source 116 is below a specified level.

FIG. 5 is a schematic diagram of an embodiment of a needleless injector system 500 including an auxiliary unit that is not physically coupled to a needleless injector unit.

The needleless injector system 500 includes many of the same components as the needleless injector systems 100, 300, and 400 shown in FIGS. 1A through 4B. Therefore, in the interest of brevity, components of the needleless injector systems 100, 300, 400, and 500 that are identical or similar to each other have been provided with the same reference numerals, and an explanation of their structure and function will not be repeated unless the components function differently in the needleless injector systems 100, 300, 400 and 500. However, it should be noted that the principles of the needleless injector system 500 are employed with any of the embodiments described with respect to FIGS. 1A through 4B.

The needleless injector system 500 includes the needleless injector unit 102 including the nozzle portion 104 positionable at or near the skin surface 106 of the subject. The needleless injector unit 102 may also include the supply 108 of one or more substances 110. The needleless injector unit 102 is configured to inject the one or more substances 110 from the nozzle portion 104 and through the skin surface 106 of the subject. The needleless injector system 500 further includes an auxiliary unit 514 operably coupleable to the needleless injector unit 102. In an embodiment, the auxiliary unit 514 includes a source 516 of one or more protectants 518 and is configured to emit the one or more protectants 518 to a region between the nozzle portion 104 and the skin surface 106. In an embodiment, the auxiliary unit 514 is configured to emit the one or more protectants 518 to protect at least the nozzle portion 104 of the needleless injector unit 102 from one or more contaminants. In an embodiment, the auxiliary unit 514 is operably coupleable with one or more different needleless injector units.

A control unit 520 including electrical control circuitry (not shown), along with a user interface 522 (e.g., a touchscreen, keypad, etc.) for user input, is provided. The control unit 520 is operably coupled to the needleless injector unit 102. In an embodiment, the control unit 520 is coupled to the auxiliary unit 514. The control unit 520 is configured to control operation of one or more of the foregoing system components. For example, the nozzle portion 104 of the needleless injector unit 102 is positioned at least proximate to a target region 124 on the skin surface 106. One or more injection-information signals 126 are output from the needleless injector unit 102 to the control unit 520 that encode injection information. In an embodiment, responsive to the one or more injection-information signals 126, the control unit 520 outputs one or more protectant emitting instructions 128 to the auxiliary unit 514. The auxiliary unit 514 emits the one or more protectants 518 in accordance with the one or more protectant emitting instructions 128.

In an embodiment, the control unit 520 outputs one or more injection-information signals 126 to the needleless injector unit 102 that encode injection information or directions. Responsive, the one or more injection-information signals 126, the needleless injector unit 102 injects at least one of the one or more substances 110 from the nozzle portion 104 and transdermally through the skin surface 106. The control unit 520 can also output one or more protectant emitting instructions 128 to the auxiliary unit 514. In an embodiment, the auxiliary unit 514 emits in the one or more protectants 518 in accordance with the protectant emitting instructions 128 to protect at least the nozzle portion 104 of the needleless injector unit 102. Thus, the control unit 520 is configured to control operation of both the needleless injector unit 102 and the auxiliary unit 514.

Figure 6:
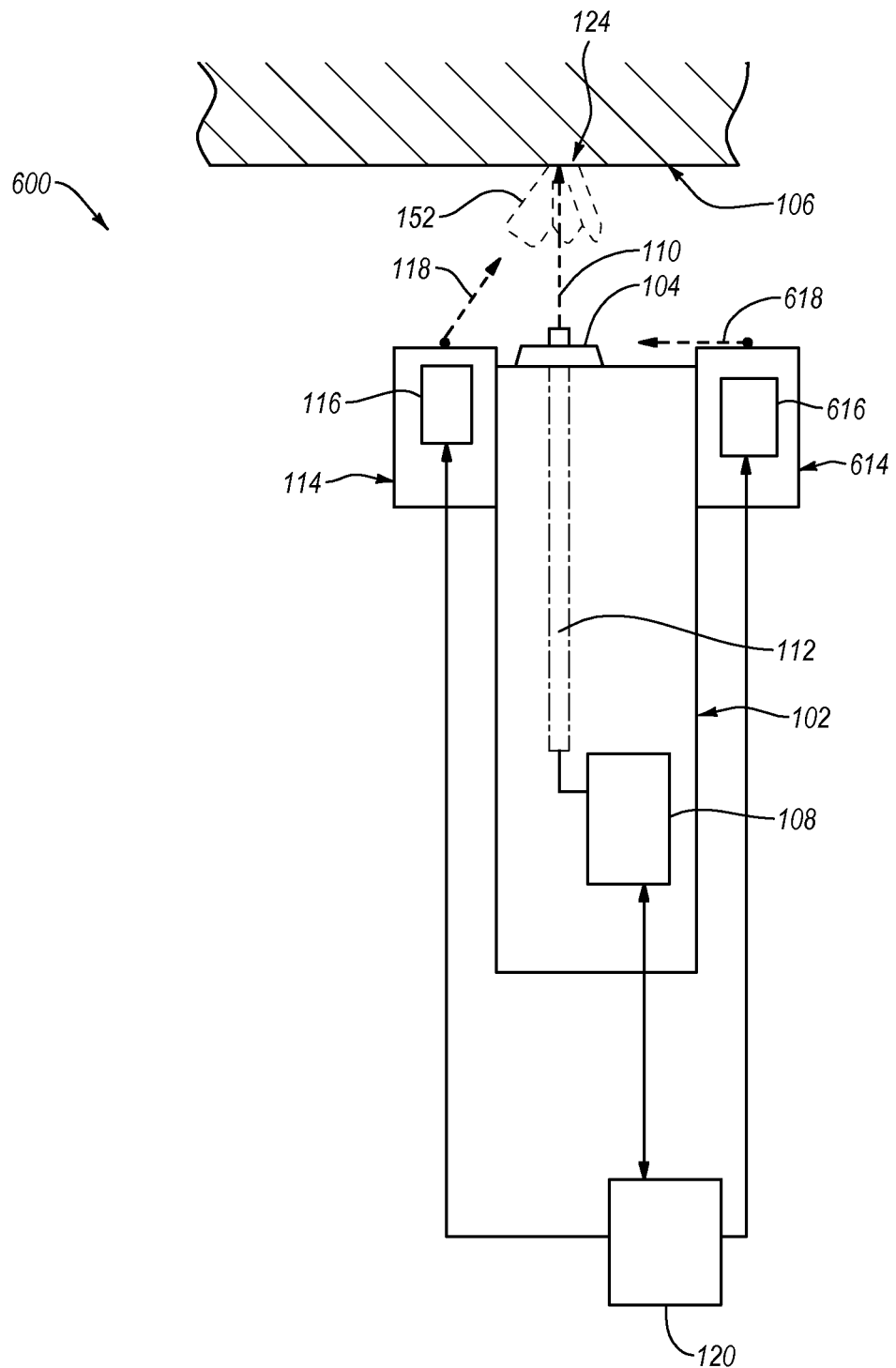
FIG. 6 is a schematic diagram of an embodiment of a needleless injector system including a plurality of auxiliary units.

FIG. 6 is a schematic diagram of an embodiment of a needleless injector system 600 including a plurality of auxiliary units, such as two or more, or three or more auxiliary units. The needleless injector system 600 includes many of the same components as the needleless injector systems 100, 300, 400 and 500 shown in FIGS. 1A through 5. Therefore, in the interest of brevity, components of the needleless injector systems 100, 300, 400, 500, and 600 that are identical or similar to each other have been provided with the same reference numerals, and an explanation of their structure and function will not be repeated unless the components function differently in the needleless injector systems 100, 300, 400, 500, and 600. However, it should be noted that the principles of the needleless injector system 600 are employed with any of the embodiments described with respect to FIGS. 1A through 5.

The needleless injector system 600 includes the needleless injector unit 102 having the nozzle portion 104 positionable at or near the skin surface 106 of the subject. The needleless injector system 100 further includes a first auxiliary unit 114 coupleable to the needleless injector unit 102. The first auxiliary unit 114 includes a first source 116 of one or more protectants 118 and is configured to emit the one or more protectants 118 to a first region between the nozzle portion 104 and the skin surface 106. In an embodiment, the first auxiliary unit 114 is configured to emit the one or more protectants 118 to protect at least the nozzle portion 104 of the needleless injector unit 102. The needleless injector system 100 further includes a second auxiliary unit 614 coupleable to the needleless injector unit 102. The second auxiliary unit 614 may include a second source 616 of one or more protectants 618 and is configured to emit the one or more protectants 618 to a second region between the nozzle portion 104 and the skin surface 106. In an embodiment, the second auxiliary unit 614 is configured to emit the one or more protectants 618 to protect at least the nozzle portion 104 of the needleless injector unit 102. In an embodiment, the first region and the second region can be substantially the same. In an embodiment, the first region and the second region can be different from one another.

A control unit 120 including control electrical circuitry (not shown) is provided. The control unit 120 is operably coupled to the needleless injector unit 102 and the first auxiliary unit 114 and the second auxiliary unit 614 to control operation of the foregoing system components. For example, the control unit 120 is configured to control operation of the needleless injector unit 102, the first auxiliary unit 114, and the second auxiliary unit 614 independent from one another or substantially simultaneously. In an embodiment, the control unit 120 is configured to direct the first auxiliary unit 114 to emit one or more protectants 118 to deflect, intercept, disperse, entrap or entrain, sterilize, irradiate, or neutralize one or more contaminants 152. The control unit 120 may further be configured to direct the second auxiliary unit 614 to emit the one or more protectants 618 to sterilize or clean the nozzle portion 104. In an embodiment, the control unit 120 is configured to direct the first auxiliary unit 114 to emit the one or more protectants 118 in a first direction. The control unit 120 may further be configured to direct the second auxiliary unit 614 to emit the one or more protectants 618 in a second direction different than the first direction. In an embodiment, the control unit 120 is configured to direct the first auxiliary unit 114 to emit the one or more protectants 118 based on feedback from the needleless injector unit 102. The control unit 120 may further be configured to direct the second auxiliary unit 614 to emit the one or more protectants 618 based on feedback or one or more sensing signals from one or more sensors.

The reader will recognize that the state of the art has progressed to the point where there is little distinction left between hardware and software implementations of aspects of systems; the use of hardware or software is generally (but not always, in that in certain contexts the choice between hardware and software can become significant) a design choice representing cost vs. efficiency tradeoffs. The reader will appreciate that there are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; alternatively, if flexibility is paramount, the implementer may opt for a mainly software implementation; or, yet again alternatively, the implementer may opt for some combination of hardware, software, and/or firmware. Hence, there are several possible vehicles by which the processes and/or devices and/or other technologies described herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary. The reader will recognize that optical aspects of implementations will typically employ optically-oriented hardware, software, and or firmware.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, the reader will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a wired communications link, a wireless communication link, etc.).

In a general sense, the various embodiments described herein can be implemented, individually and/or collectively, by various types of electro-mechanical systems having a wide range of electrical components such as hardware, software, firmware, or virtually any combination thereof; and a wide range of components that may impart mechanical force or motion such as rigid bodies, spring or torsional bodies, hydraulics, and electro-magnetically actuated devices, or virtually any combination thereof. Consequently, as used herein "electro-mechanical system" includes, but is not limited to, electrical circuitry operably coupled with a transducer (e.g., an actuator, a motor, a piezoelectric crystal, etc.), electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), electrical circuitry forming a communications device (e.g., a modem, communications switch, or optical-electrical equipment), and any non-electrical analog thereto, such as optical or other analogs. Those skilled in the art will also appreciate that examples of electro-mechanical systems include but are not limited to a variety of consumer electronics systems, as well as other systems such as motorized transport systems, factory automation systems, security systems, and communication/computing systems. Those skilled in the art will recognize that electro-mechanical as used herein is not necessarily limited to a system that has both electrical and mechanical actuation except as context may dictate otherwise.

In a general sense, the various aspects described herein which can be implemented, individually and/or collectively, by a wide range of hardware, software, firmware, or any combination thereof can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). The subject matter described herein may be implemented in an analog or digital fashion or some combination thereof.

The herein described components (e.g., steps), devices, and objects and the discussion accompanying them are used as examples for the sake of conceptual clarity. Consequently, as used herein, the specific exemplars set forth and the accompanying discussion are intended to be representative of their more general classes. In general, use of any specific exemplar herein is also intended to be representative of its class, and the non-inclusion of such specific components (e.g., steps), devices, and objects herein should not be taken as indicating that limitation is desired.

With respect to the use of substantially any plural and/or singular terms herein, the reader can translate from the plural to the singular and/or from the singular to the plural as is appropriate to the context and/or application. The various singular/plural permutations are not expressly set forth herein for sake of clarity.

The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected," or "operably coupled," to each other to achieve the desired functionality, and any two components capable of being so associated can also be viewed as being "operably couplable," to each other to achieve the desired functionality. Specific examples of operably couplable include but are not limited to physically mateable and/or physically interacting components and/or wirelessly interactable and/or wirelessly interacting components and/or logically interacting and/or logically interactable components.

In some instances, one or more components may be referred to herein as "configured to." The reader will recognize that "configured to" can generally encompass active-state components and/or inactive-state components and/or standby-state components, etc. unless context requires otherwise.

While particular aspects of the present subject matter described herein have been shown and described, it will be apparent that, based upon the teachings herein, changes and modifications may be made without departing from the subject matter described herein and its broader aspects and, therefore, the appended claims are to encompass within their scope all such changes and modifications as are within the true spirit and scope of the subject matter described herein. Furthermore, it is to be understood that the invention is defined by the appended claims. In general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense the convention (e.g., "a system having at least one of A, B, or C" would include but not be limited to systems that have A alone, B alone, C alone, A and B together, A and C together, B and C together, and/or A, B, and C together, etc.). Virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

With respect to the appended claims, the recited operations therein may generally be performed in any order. Examples of such alternate orderings may include overlapping, interleaved, interrupted, reordered, incremental, preparatory, supplemental, simultaneous, reverse, or other variant orderings, unless context dictates otherwise. With respect to context, even terms like "responsive to," "related to," or other past-tense adjectives are generally not intended to exclude such variants, unless context dictates otherwise.

While various aspects and embodiments have been disclosed herein, the various aspects and embodiments disclosed herein are for purposes of illustration and are not intended to be limiting, with the true scope and spirit being indicated by the following claims.

What is claimed is:

1. A needleless injector system, comprising:
a needleless injector unit having a nozzle portion and a supply of one or more substances for injection, the needleless injector unit configured to inject the one or more substances from the nozzle portion through a target region including a skin surface of a subject;
an auxiliary unit coupleable to the needleless injector unit and having a source of one or more protectants the auxiliary unit configured to emit the one or more protectants in a region between the nozzle portion of the needleless injector unit and the skin surface of the subject;
one or more sensors configured to,
detect one or more characteristics of at least one of the one or more contaminants, the nozzle portion, the target region, or the one or more substances; and
second one or more sensing signals encoding the detected one or more characteristics; and
a control unit operably coupled to the one or more sensors to receive the one or more sensing signals from the one or more sensors and configured to send an activation signal to the auxiliary unit that directs the auxiliary unit to emit the one or more protectants responsive to the one or more sensing signals.

2. The needleless injector system of claim 1, wherein the one or more protectants protect at least the nozzle portion of the needleless injector unit from one or more contaminants, and wherein the one or more contaminants include at least one of a biological material, a molecule, a hazardous material, blood, cellular debris, a cell, a biological fluid, bacteria, a virus, or a medication.

3. The needleless injector system of claim 2, wherein the auxiliary unit is configured to emit at least one of the one or more protectants to substantially disperse the one or more contaminants.

4. The needleless injector system of claim 2, wherein the auxiliary unit is configured to emit at least one of the one or more protectants to substantially deflect the one or more contaminants away from the nozzle portion.

5. The needleless injector system of claim 2, wherein the auxiliary unit is configured to emit at least one of the one or more protectants to substantially intercept the one or more contaminants.

6. The needleless injector system of claim 2, wherein at least one of the one or more protectants substantially sterilizes the one or more contaminants.

7. The needleless injector system of claim 2, wherein the auxiliary unit is configured to emit at least one of the one or more protectants as electromagnetic radiation that substantially irradiates the one or more contaminants.

8. The needleless injector system of claim 2, wherein at least one of the one or more protectants substantially neutralizes the one or more contaminants.

9. The needleless injector system of claim 2, wherein at least one of the one or more protectants substantially entraps or entrains the one or more contaminants.

10. The needleless injector system of claim 2, wherein the one or more characteristics include at least one of presence, position, or direction of the one or more contaminants of the one or more substances.

11. The needleless injector system of claim 10, wherein the activation signal directs the auxiliary unit to emit at least one of the one or more protectants in one or more timed intervals.

12. The needleless injector system of claim 10, wherein the activation signal directs the auxiliary unit to emit at least one of the one or more protectants in one or more waves.

13. The needleless injector system of claim 10, wherein the one or more sensors include at least one of an ultrasound sensor, a pressure sensor, a light sensor, a piezoelectric sensor, a motion sensor, a position sensor, a flows sensor, a viscosity sensor, an imaging detector, an acoustic sensor, a temperature sensor, a chemical detector, a transceiver, or an electromagnetic energy detector.

14. The needleless injector system of claim 10, wherein the one or more sensors mounted on the auxiliary unit.

15. The needleless injector system of claim 10, wherein the control unit includes processing circuitry and one or more application software programs configured correlate the one or more detected characteristics with one or more known characteristics of the one or more substances or the one or more contaminants.

16. The needleless injector system of claim 1, wherein the source of the one or more protectants includes an electromagnetic radiation source configured to output electromagnetic radiation.

17. The needleless injector system of claim 16, wherein the electromagnetic radiation includes ultraviolet electromagnetic radiation or infrared electromagnetic radiation.

18. The needleless injector system of claim 1, wherein at least one of the one or more protectants includes at least one of a disinfectant, an oxidizer, an acid, a base, an adhesive, or a neutralizer.

19. The needleless injector system of claim 1, wherein at least one of the one or more protectants includes pressurized air.

20. The needleless injector system of claim 1, wherein at least one of the one or more protectants includes water.

21. The needleless injector system of claim 1, wherein at least one of the one or more protectants substantially disinfects or cleans the nozzle portion of the needleless injector unit.

22. The needleless injector system of claim 21, wherein the at least one of the one or more protectants includes at least one of sodium hypochlorite, hydrogen peroxide, or chlorhexidine.

23. The needleless injector system of claim 1, wherein the auxiliary unit includes an articulating nozzle configured to articulate to control a direction that the one or more protectants are emitted therefrom.

24. The needleless injector system of claim 23, wherein the control unit is operably coupled to the articulating nozzle and configured to direct articulation of the articulating nozzle responsive to the one or more sensing signals.

25. The needleless injector system of claim 1, wherein the control unit is configured to direct the auxiliary unit to emit at least one of the one or more protectants before the needleless injector unit injects the one or more substances.

26. The needleless injector system of claim 1, wherein the control unit is configured to direct the auxiliary unit to emit at least one of the one or more protectants after the needleless injector unit injects the one or more substances.

27. The needleless injector system of claim 1, wherein the control unit is configured to direct the auxiliary unit to emit at least one of the one or more protectants responsive to the needleless injector unit injecting the one or more substances.

28. The needleless injector system of claim 1, wherein the auxiliary unit includes a fluid dispensing unit having a source of at least one of the one or more protectants.

29. The needleless injector system of claim 1, wherein the auxiliary unit includes an electromagnetic radiation source configured to output electromagnetic radiation that constitutes at least one of the one or more protectants.

30. The needleless injector system of claim 1, wherein the auxiliary unit includes a fluid dispensing unit having a source of at least one of the one or more protectants and an electromagnetic radiation source configured to output electromagnetic radiation that constitutes at least one of the one or more protectants.

31. The needleless injector system of claim 1, wherein the control unit controls operation of at least one of the needleless injector unit or the auxiliary unit.

32. The needleless injector system of claim 1, further comprising one or more interlocks that prevent injection of the one or more substances from the nozzle portion when the auxiliary unit is not coupled to the needleless injector unit.

33. The needleless injector system of claim 1, wherein the coupling mechanism includes one or more interlocks that prevent injection of the one or more substances from the nozzle portion when the source of the one or more protectants is below a predetermined level.

34. The needleless injector system of claim 1, wherein the needleless injector unit is configured to inject the one or more substances intradermally through the skin surface of the subject.

35. The needleless injector system of claim 1, wherein the needleless injector units is configured to inject the one or more substances transdermally through the skin surface of the subject.

36. The needleless injector system of claim 1, wherein the one or more substances includes a fluid.

37. The needleless injector system of claim 1, wherein the needleless injection unit is configured to inject the one or more substances from the nozzle portion with sufficient injection pressure to penetrate through the skin surface of the subject.

38. The needleless injector system of claim 1, further comprising a coupling mechanism that physically couples the needleless injector to the auxiliary unit.

39. The needleless injector system of claim 1, wherein at least one of the one or more protectants includes at least one of a gas, a liquid, or a solid phase material.

40. The needleless injector system of claim 1, wherein, when the auxiliary unit is physically coupled to the needleless injector using the coupling mechanism, the auxiliary unit is configured to emit at least one of the one or more protectants in a first direction and the needleless injector unit is configured to emit at least one of the one or more of the substances in a second direction that is different than the first direction.

41. The needleless injector system of claim 1, wherein the auxiliary unit includes a dispensing unit and a nozzle, the dispensing unit operably coupled to the source of the one or more protectants and the nozzle operably coupled to the dispensing unit, the dispensing unit and the nozzle of the auxiliary unit configured to emit the one or more protectants in the region between the nozzle portion of the needleless injector unit and the skin surface of the subject.

42. The needleless injector system of claim 1, wherein the dispensing unit includes at least one of a fluid dispensing unit, a force generating mechanism, an actuator, a piston, or a pump.

43. A needleless injector system, comprising:
a needleless injector unit having a nozzle portion and a supply of one or more substances for injection, the one or more substances including a fluid, the needleless injector unit configured to inject the one or more substances from the nozzle portion through a target region including a skin surface of a subject;
an auxiliary unit coupleable to the needleless injector unit and having a source of one or more protectants, the auxiliary unit configured to emit the one or more protectants in a region between the nozzle portion of the needleless injector unit and the skin surface of the subject;
one or more sensors configured to,
    detect one or more characteristics of at least one of one or more contaminants, the nozzle portion, the target region, or the one or more substances, wherein the one or more characteristics include at least one of presence, position, or direction of the one or more contaminants or the one or more substances; and
    send one or more sensing signals encoding the detected one or more characteristics; and
a control unit operably coupled to the one or more sensors to receive the one or more sensing signals from the one or more sensors and configured to send an activation signal to the auxiliary unit that directs the auxiliary unit to emit the one or more protectants responsive to the one or more sensing signals.

44. The needleless injector system of claim 40, wherein the first direction is substantially oblique to the skin surface of the subject, and wherein the second direction is substantially perpendicular to the skin surface of the subject.

45. The needleless injector system of claim 40, wherein the first direction is substantially parallel the skin surface of the subject.

\* \* \* \* \*

UNITED STATES PATENT AND TRADEMARK OFFICE
CERTIFICATE OF CORRECTION

PATENT NO. : 9,808,579 B2
APPLICATION NO. : 13/889438
DATED : November 7, 2017
INVENTOR(S) : Roderick A. Hyde et al.

It is certified that error appears in the above-identified patent and that said Letters Patent is hereby corrected as shown below:

In the Claims

In Column 23, Claim 15, Line 57 delete "more application software programs configured correlate the" and insert --more application software programs configured to correlate the--, therefor.

In Column 26, Claim 45, Line 34 delete "the first direction is substantially parallel the skin surface of" and insert --the first direction is substantially parallel to the skin surface of--, therefor.

Signed and Sealed this
Tenth Day of July, 2018

Andrei Iancu
*Director of the United States Patent and Trademark Office*